US012746286B2

(12) United States Patent
Gan et al.

(10) Patent No.: US 12,746,286 B2
(45) Date of Patent: Sep. 29, 2026

(54) LONG-ACTING ROPIVACAINE PHARMACEUTICAL COMPOSITION, PREPARATION METHOD THEREFOR AND USE THEREOF

(71) Applicant: SHANGHAI INSTITUTE OF MATERIA MEDICA, CHINESE ACADEMY OF SCIENCES, Shanghai (CN)

(72) Inventors: Yong Gan, Shanghai (CN); Shiyan Guo, Shanghai (CN); Yinyin Sun, Shanghai (CN); Quanlei Zhu, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 1098 days.

(21) Appl. No.: 17/792,474

(22) PCT Filed: Jan. 14, 2021

(86) PCT No.: PCT/CN2021/071647
§ 371 (c)(1),
(2) Date: Sep. 8, 2022

(87) PCT Pub. No.: WO2021/143745
PCT Pub. Date: Jul. 22, 2021

(65) Prior Publication Data

US 2023/0080811 A1 Mar. 16, 2023

(30) Foreign Application Priority Data

Jan. 14, 2020 (CN) ......................... 202010037064.4

(51) Int. Cl.

| | |
|---|---|
| ***A61K 31/277*** | (2006.01) |
| ***A61K 9/08*** | (2006.01) |
| ***A61K 31/445*** | (2006.01) |
| ***A61K 47/12*** | (2006.01) |
| ***A61K 47/24*** | (2006.01) |
| ***A61K 47/44*** | (2017.01) |
| ***A61P 23/02*** | (2006.01) |

(52) U.S. Cl.
CPC ................ *A61K 47/24* (2013.01); *A61K 9/08* (2013.01); *A61K 31/445* (2013.01); *A61K 47/12* (2013.01); *A61K 47/44* (2013.01); *A61P 23/02* (2018.01)

(58) Field of Classification Search
None
See application file for complete search history.

(56) References Cited

U.S. PATENT DOCUMENTS

| | | | |
|---|---|---|---|
| 9,849,088 | B2 | 12/2017 | Amselem et al. |
| 10,213,510 | B2 | 2/2019 | Ottoboni et al. |
| 11,364,299 | B2 | 6/2022 | Chen et al. |
| 2015/0250724 | A1 | 9/2015 | Yamashita et al. |
| 2015/0359738 | A1 | 12/2015 | Mulvahill |

FOREIGN PATENT DOCUMENTS

| | | | | | |
|---|---|---|---|---|---|
| CN | 102370619 | A | | 3/2012 | |
| CN | 103142458 | B | | 9/2015 | |
| CN | 106535886 | A | | 3/2017 | |
| CN | 104427977 | B | | 2/2018 | |
| CN | 108159055 | A | * | 6/2018 | ........... A61K 9/0019 |
| CN | 108743952 | A | * | 11/2018 | ............. A61K 47/44 |
| CN | 109316602 | A | | 2/2019 | |
| EP | 3927410 | A1 | * | 12/2021 | |
| TW | I626061 | B | * | 6/2018 | .............. A61P 35/04 |
| WO | WO-2008089822 | A2 | * | 7/2008 | .............. A61P 43/00 |
| WO | 2013168172 | A1 | | 11/2013 | |
| WO | 2019046293 | A1 | | 3/2019 | |

OTHER PUBLICATIONS

International Search Report issued in corresponding International Application No. PCT/CN2021/071647 dated Apr. 21, 2021, pp. 1-3, English Translation.

Sekimoto, K. et al., “Local anesthetic toxicity: acute and chronic management” Acute Medicine & Surgery (Apr. 2017) pp. 152-160, vol. 4, No. 2.

Sekimoto, K. et al., “Tetracaine at a Small Concentration Delayed Nerve Growth Without Destroying Neurites and Growth Cones” Anesth Analg. (Sep. 2006) pp. 608-614, vol. 103, No. 3.

“Seaweed Oil” BAIdu, https://baike.baidu.com/item/紫菜油/6397286, accessed on Mar. 11, 2026 with English translation.

“Porphyra” Wikipedia, https://en.wikipedia.org/wiki/Porphyra, accessed on Mar. 11, 2026.

“Porphyra umbilicalis” Wikipedia, https://en.wikipedia.org/wiki/Porphyra_umbilicalis, accessed on Mar. 11, 2026.

(Continued)

*Primary Examiner* — Layla Soroush

(74) *Attorney, Agent, or Firm* — Carter, DeLuca & Farrell LLP

(57) ABSTRACT

Provided are a long-acting ropivacaine pharmaceutical composition, a preparation method therefor and use thereof. The pharmaceutical composition comprises: ropivacaine; a pharmaceutical solvent; a pharmaceutical phospholipid; a pharmaceutical oil; and an efficacy enhancer, an optional antioxidant and an optional acid-base regulator. The pharmaceutical composition has a controllable release behavior and a sustained release effect, can significantly reduce the peak plasma concentration of the drug, maintain a stable plasma concentration in the body, prolong the effective treatment time, reduce the effective therapeutic dose, improve the utilization of the drug, and reduce the risk of neurotoxicity. The pharmaceutical composition has a long-acting analgesic effect and can be used for pain treatment.

14 Claims, 10 Drawing Sheets

(56) References Cited

OTHER PUBLICATIONS

Naudi, A. et al., "Region Specific Vulnerability to Lipid Peroxidation in the Human Central Nervous System" INTECH (Aug. 2012), pp. 1-20, Chapter 20, http://dx.doi.org/10.5772/46022.

Guitard, R., "Oxidation of Omega-3 Oils and Preservation by Natural Phenolic Antioxidants" Chemistry (Oct. 2016) with English translation.

* cited by examiner

Composition 8

Comparative Example 7

LONG-ACTING ROPIVACAINE PHARMACEUTICAL COMPOSITION, PREPARATION METHOD THEREFOR AND USE THEREOF

CROSS REFERENCE TO RELATED APPLICATIONS

The present application is a national stage application of International Application No. PCT/CN2021/071647, filed Jan. 14, 2021, which claims the benefit of and priority to Chinese Patent Application No. 202010037064.4, filed Jan. 14, 2020, the entire contents of each of which are hereby incorporated by reference herein in their entirety.

TECHNICAL FIELD

The invention belongs to the field of medical technology, and in particular relates to a long-acting ropivacaine pharmaceutical composition, a preparation method therefor, and a use thereof for preparing a medicament for treating postoperative pain. The pharmaceutical composition has a controllable release behavior and a sustained release effect, can significantly reduce the peak plasma concentration of the drug, maintain a stable plasma concentration in the body, prolong the effective treatment time, reduce the effective therapeutic dose, improve the utilization of the drug, and reduce the risk of neurotoxicity. The pharmaceutical composition has a long-acting analgesic effect and can be used for treating postoperative pain.

BACKGROUND ART

Postoperative pain is a comprehensive response to soft tissue trauma during hypersensitivity surgery that stimulates the central nervous system. It belongs to acute pain and will have a significant impact on the patient's various organ functions, causing changes in a series of pathophysiological parameters and leading to various complications, which seriously affects the postoperative rehabilitation of the patient, and affects the life and health of the patient.

Postoperative analgesia can not only reduce the patient's postoperative pain, but also stabilize his various physiological indicators, reduce the probability of complications during surgery, improve prognosis and have a significant impact on shortening the length of hospital stay.

Local anesthetics can reversibly block the occurrence and conduction of nerve impulses at the applied site by inhibiting the sodium channels in nerve cells, and are often used for analgesia in clinical practice.

Ropivacaine is an amide local anesthetics newly synthesized in recent years, which is the result of further optimization of bupivacaine. Compared with traditional local anesthetics, ropivacaine has the advantages of longer therapeutic time, exact pain treatment effect, and less cardiotoxicity, suggesting that its clinical application will be more extensive in the future.

Ropivacaine has a basic structure of the levorotatory isomer of 1-propyl-2,6-piperidine amide hydrochloride with a pH of 7.4 and a pKa of 8.1, and has a low lipid solubility and a high dissociation constant. Therefore, it has significantly higher sensitivity to C-fiber than that to A-fiber, and it has the characteristics of obvious separation of motor nerve block and sensory nerve block, that is, it produces only the sensory nerve block and has a minimal and non-progressive impact on the motor nerve block at a low concentration; and it produces the motor nerve block and the sensory nerve block at a high concentration. Modern anesthesia theory believes that maintaining a certain exercise capacity of the patient (that is, reducing the occurrence of motor block) while fully analgesic after surgery is conducive to early ambulation, promotes peristalsis of the gastrointestinal tract and functional recovery, and can shorten the length of hospital stay. More importantly, the high drug concentration accompanying with motor block may cause chronic neurotoxicity (Acute Med Surg. 2017 April; 4(2): 152-160). Therefore, increasing the sensory nerve block while avoiding motor block as much as possible has important clinical significance.

At present, the clinical preparation of ropivacaine is relatively simple, only ordinary aqueous hydrochloride or mesylate solution exists, and the action time is short, which is difficult to meet the treatment requirements of postoperative pain. However, multiple administration of ropivacaine will not only lead to patient's poor compliance, but also cause the peak-valley effect of plasma concentration, resulting in toxic reactions. Therefore, the development of a safe and long-acting ropivacaine pharmaceutical composition has important clinical application value.

CN103142458B provides a ropivacaine oil solution preparation composition, which has a simple formulation process and a certain sustained-release effect. The pharmaceutical composition involved in the examples is a system composed of ropivacaine dissolved in benzyl alcohol, benzyl benzoate, soybean oil or castor oil. But upon investigation, the composition can cause an inflammatory reaction at the injection site, which may bring the risk of neuroinflammation; and it has a certain risk of local irritation, which is a safety hazard.

CN104427977B provides a proliposome preparation of ropivacaine hydrochloride comprising a natural phospholipid, a non-aqueous carrier and a viscosity modifier ethanol, and a preparation method thereof. The proliposome preparation has improved drug loading capacity, and prolonged duration of action. However, the preparation has high viscosity and poor syringeability, which brings inconvenience to clinical use. Meanwhile, it has low effective bioavailability, which will lead to the waste of the drug.

CN109316602A provides a compound sustained-release drug delivery system composed of a local anesthetic, a non-steroidal anti-inflammatory drug, a solvent and a sustained-release material. Although it has a certain sustained-release analgesic effect and the function of promoting wound healing, the non-steroidal anti-inflammatory drug has a ceiling effect and has the disadvantages of easily causing adverse reactions in the gastrointestinal tract and neurological and cardiovascular toxicity. Meanwhile, the proportion of the organic solvent is relatively large, reaching 30-40%, which is easy to cause irritation at the injection site and has potential safety hazards.

CN108743952A provides a local anesthetic sustained-release preparation with a phospholipid-a miscible solvent-an oil as a carrier and a preparation method, wherein benzyl benzoate, ethanol and benzyl alcohol are used as the solvent, and the total amount of the solvent is as high as 40-50%, which is easy to cause irritation at the injection site and systemic adverse reactions, and thus there are potential safety hazards.

WO2019046293A1 provides a sustained-release anesthetic composition comprising a local anesthetic and one or more lipid mixtures (such as phospholipid or cholesterol), which is formed by preparing a lipid matrix through a one-step lyophilization method, and then hydrating with a buffer. US2015250724A1 provides a long-acting controlledrelease local anesthetic liposome preparation, wherein a liposome composition is obtained by mixing water and an organic phase, adding a phospholipid and cholesterol to form an emulsion, and subjecting the emulsion to external solution exchange with a second aqueous phase solution. The preparation processes of the above-mentioned two patents are relatively complex and have stability problems when stored for a long time.

CN106535886A provides a drug delivery system composed of an amide-type local anesthetic, an enolic acid non-steroidal anti-inflammatory drug and a delivery vehicle for the treatment of acute or chronic pain. Likewise, the non-steroidal anti-inflammatory drug has the ceiling effect and has the disadvantages of easily causing adverse reactions in the gastrointestinal tract and neurological and cardiovascular toxicity. In addition, the delivery vehicle is composed of polyorthoesters, a polar aprotic solvent and the viscosity reducing agent triglyceride, and the obtained composition has high viscosity, poor syringeability and poor clinical administration convenience.

In addition, as reported in *Anesth Analg*. 2006 September; 103 (3): 608-14, when nerve fibers are exposed to a local anesthetics at low concentration for a long time, the growth of neurites is significantly delayed, and the axonal transport of actin is disrupted, causing damage to nerve fibers and resulting in symptoms such as neuroinflammation or neurofibrosis.

So far, all of the above patent documents adopt the commonly used auxiliary materials. Although the obtained composition has a certain sustained-release effect, it has the disadvantages of low drug effective availability, high irritation at the injection site, high potential safety hazards, poor syringeability, complicated processes, and poor stability. The composition of the present invention made improvements on the basis of the existing research technology. By adding an appropriate amount of an efficacy enhancer, the present invention can not only maintain the characteristics of sustained-release effect and good stability of the composition, but also prolong the duration of action of the conventional sustained-release preparation at the same dosage. It can also reduce the effective therapeutic dose under the same analgesic effect, improve the motor nerve block condition, and improve the drug safety, which has not been reported in this field.

DISCLOSURE OF INVENTION

An object of the present invention is to provide a long-acting ropivacaine pharmaceutical composition.

Another object of the present invention is to provide a preparation method of the above-mentioned long-acting ropivacaine pharmaceutical composition.

Still another object of the present invention is to provide the use of the above-mentioned long-acting ropivacaine pharmaceutical composition.

After investigation, the inventors learned that an oil solution can provide an improved sustained-release effect. However, the salt of ropivacaine has poor solubility in the oil, which cannot meet the needs of clinical high-dose administration. After trials, the inventors found that, by adding an appropriate amount of a pharmaceutical phospholipid to the composition, and carrying out a suitable preparation process, both the ropivacaine salt and ropivacaine free base can be dissolved, and the solution has good stability and syringeability for injection.

Based on this, the inventors prepared compositions comprising different proportions of a pharmaceutical phospholipid, and carry out in vivo pharmacodynamic investigations in rats. Surprisingly, the inventors found that, when the obtained compositions have different proportions of the phospholipid, they have different in vivo duration of action in rats, but all of them have significantly prolonged duration of action compared with ropivacaine hydrochloride injection (trade name: Naropin). Therefore, in drug development, it is possible to design a composition according to different clinical treatment needs to achieve the purpose of precise treatment.

Although the above composition significantly reduces the peak plasma concentration compared with ropivacaine hydrochloride injection and has a certain sustained-release effect, the inventors found that the drug in the composition is not completely released in vivo in rats, resulting in poor bioavailability, especially effective bioavailability.

The drugs that have not exerted their effect will remain in the body, which not only causes drug waste, but may also cause chronic toxicity to nerve fibers. Meanwhile, during the whole pharmacohynamic determination, there was a phenomenon that the rat's feet curled up without touching the ground for a long time (i.e. motor block), so the research and development of the composition needs to be improved.

In the present invention, the effective therapeutic dose R is calculated by the following formula:

$$R=A/T_t$$

wherein A is the administration dose of ropivacaine, and $T_t$ is the effective treatment time of the drug in the body. Here, the effective treatment time of the drug in the body refers to the duration of action, which is determined by pharmacodynamic experiments. The smaller the R value is, the smaller the drug dose required to achieve the unit duration of action, that is, the longer the effective treatment time of the drug at the same dose.

Through research, the inventors surprisingly found that, by adding the efficacy enhancer of the present invention, the duration of action of the pharmaceutical composition is significantly prolonged, the effective bioavailability is improved, the analgesic effect is enhanced, and the R value of the effective therapeutic dose is significantly decreased, and the irritation at the injection site is significantly reduced, and under the same analgesic effect, the motor block is significantly improved.

Based on the above research, the present invention provides a long-acting ropivacaine pharmaceutical composition, which has obvious advantages over ropivacaine hydrochloride injection and other reported preparations in terms of safety, sustained-release effect and maintenance time, drug utilization, improvement of motor block and the like.

In one aspect, the present invention provides a long-acting ropivacaine pharmaceutical composition comprising ropivacaine; a pharmaceutical solvent; a pharmaceutical phospholipid; a pharmaceutical oil; an efficacy enhancer; an optional antioxidant and an optional acid-base regulator, wherein the efficacy enhancer can significantly prolong the duration of action of the composition, and can significantly reduce the effective therapeutic dose of the drug compared with conventional sustained-release preparations at the same dose, preferably, the efficacy enhancer is one or a combination of two or more selected from the group consisting of an ω-3 fatty acids and metabolites thereof, and substances rich in ω-3 fatty acids or metabolites thereof, etc., more preferably, the amount of the efficacy enhancer in the composition ranges from 0.5% to 10%.

Preferably, the composition of the present invention comprises, based on the total weight of the composition, in weight percentage,

- about 0.5% to about 10%, preferably about 1% to about 8%, more preferably about 1% to about 5% of ropivacaine;
- about 2% to about 25%, preferably about 3% to about 23%, more preferably about 5% to about 20% of the pharmaceutical solvent;
- about 8% to about 55%, preferably about 10% to about 50%, more preferably about 15% to about 45% of the pharmaceutical phospholipid;
- about 15% to about 89%, preferably about 20% to about 76%, more preferably about 22% to about 60% of the pharmaceutical oil;
- about 0.5% to about 10%, preferably about 1% to about 9%, more preferably about 2% to about 8% of the efficacy enhancer;
- about 0% to about 1%, preferably about 0% to about 0.5%, more preferably about 0% to about 0.3% of the antioxidant;
- about 0% to about 8%, preferably about 0% to about 5%, more preferably about 0% to about 3% of the acid-base regulator.

In the pharmaceutical composition of the present invention, the ropivacaine mainly includes ropivacaine free base and its salts, and can be one or a combination of two or more of them. Preferably, the salts may be, for example, hydrochloride, mesylate, hydrobromide, hydroiodide, sulfate, citrate, tartrate, lactate, citrate, maleate, fumarate, etc.

In the pharmaceutical composition of the present invention, preferably, the pharmaceutical solvent may be a single organic solvent or a mixture of multiple organic solvents. Examples of the pharmaceutical solvent includes, but are not limited to, benzyl alcohol, ethanol, propylene glycol, glycerin, isopropanol, N-methylpyrrolidone, dimethyl sulfoxide, liquid polyethylene glycol, dimethylacetamide, glycerol monoacetate, polyethylene glycol monomethyl ether, diethylene glycol monoethyl ether, ethyl lactate, ethyl acetate, propylene glycol diethyl ester, diethyl malonate, tetrahydrofuran polyethylene glycol ether, and benzyl benzoate, or a mixture of two or more thereof, more preferably, the pharmaceutical solvent is one or more selected from the group consisting of benzyl alcohol, propylene glycol, and ethanol.

In the pharmaceutical composition of the present invention, the antioxidant is used to prevent or slow down the oxidative degradation of the composition, and it can be any antioxidant in the art that can be used in the pharmaceutical composition system of the present invention, as long as it has no obvious adverse effect on the drug activity of ropivacaine. For example, it can be one or more selected from the group consisting of cysteine, α-tocopherol, α-tocopherol acetate, N-acetyl-L-cysteine, butylated hydroxyanisole, dibutylated hydroxytoluene, propyl gallate, tert-butyl hydroquinone, lipoic acid, tea polyphenols, L-ascorbyl palmitate, and glutathione; preferably one or more selected from the group consisting of α-tocopherol and L-ascorbyl palmitate.

In the pharmaceutical composition of the present invention, the acid-base regulator is used to adjust the acid-base property of the composition, and it can be any acid-base regulator in the art that can be used in the pharmaceutical composition system of the present invention, as long as it has no obvious adverse effect on the drug activity of ropivacaine. For example, it can be one or more selected from the group consisting of arginine, lysine, histidine, glycine, tromethamine, diethanolamine, ethylenediamine, meglumine, hydrochloric acid, acetic acid, anhydrous citric acid, ascorbic acid, lactic acid, tartaric acid, methanesulfonic acid, methionine, sodium hydroxide, and triethanolamine; preferably one or more selected from the group consisting of tromethamine, diethanolamine, ethylenediamine, and meglumine.

In the pharmaceutical composition of the present invention, the pharmaceutical oil can be one or a combination of two or more selected from the group consisting of natural vegetable oils (e.g. castor oil, sesame oil, soybean oil, sunflower oil, peanut oil, corn oil, rapeseed oil, olive oil, cottonseed oil), semi-natural oils artificially modified from natural vegetable oils (e.g. hydrogenated castor oil), purified oils, and corresponding derivatives; and artificial synthesized oils, mainly including medium chain triglycerides (e.g. caprylic triglyceride, capric triglyceride, or a mixture thereof), long chain triglycerides, triacetin or other corresponding derivatives, ethyl oleate.

In the pharmaceutical composition of the present invention, the pharmaceutical phospholipid can be one or more selected from the group consisting of natural phospholipids, semi-synthetic phospholipids and synthetic phospholipids. Examples of the natural phospholipid include, but are not limited to, egg yolk lecithin, soybean phospholipid or a combination thereof. Examples of the semi-synthetic phospholipid include, but are not limited to, hydrogenated egg yolk lecithin, hydrogenated soybean phospholipid or a combination thereof. Examples of the synthetic phospholipid include, but are not limited to, one or more selected from the group consisting of dipalmitoyl phosphatidylethanolamine, dipalmitoyl phosphatidic acid, dipalmitoylphosphatidylglycerol, dioleoylphosphatidyl-ethanolamine, dipalmitoylphosphatidylcholine, distearoylphosphatidylcholine, dimyristoyl phosphatidyl choline. The pharmaceutical phospholipid is preferably a natural phospholipid.

In the pharmaceutical composition of the present invention, the efficacy enhancer can significantly prolong the duration of action of the composition, and can significantly reduce the effective therapeutic dose of the drug compared with conventional sustained-release preparations at the same dose. Preferably, the efficacy enhancer of the present invention may be one or two or more selected from the group consisting of ω-3 fatty acids and metabolites thereof, and substances rich in ω-3 fatty acids or metabolites thereof.

Specifically, the ω-3 fatty acid and metabolites thereof mainly refer to ω-3 polyunsaturated fatty acids and metabolites thereof, such as α-linolenic acid and its metabolites eicosapentaenoic acid (EPA) and docosahexaenoic acid (DHA) or a combination thereof. The α-linolenic acid involved is α-linolenic acid (ALA) of plant origin, and the substance rich in α-linolenic acid can be vegetable oils such as linseed oil, perilla seed oil, walnut oil, argan oil; the substance rich in α-linolenic acid metabolite such as EPA and DHA can be fish oil, laver oil, algae oil. The substances rich in ω-3 fatty acid or metabolite thereof include substances rich in α-linolenic acid, substances rich in α-linolenic acid metabolites eicosapentaenoic acid and docosahexaenoic acid, or combinations thereof, preferably, the substances rich in α-linolenic acid include linseed oil, perilla seed oil, walnut oil, argan oil or combinations thereof; the substances rich in the metabolites of α-linolenic acid, eicosapentaenoic acid and docosahexaenoic acid, include fish oil, laver oil, and algal oil or combinations thereof.

In the pharmaceutical composition of the present invention, preferably, the efficacy enhancer is one or more selected from the group consisting of substances rich in ω-3 fatty acid or metabolites thereof, more preferably, the efficacy enhancer is one or more selected from the group consisting of substances with an eicosapentaenoic acid content of no less than 15% and a docosahexaenoic acid content of no less than 10% among the substances rich in ω-3 fatty acids or metabolites thereof; particularly preferably, the efficacy enhancer is selected from the group consisting of substances with an eicosapentaenoic acid content of no less than 20% and a docosahexaenoic acid content of no less than 10% among the substances rich in ω-3 fatty acids or metabolites thereof, and still more particularly preferably, the efficacy enhancer is one or more selected from the group consisting of fish oil and laver oil.

The long-acting ropivacaine pharmaceutical composition of the present invention can reduce the peak plasma concentration of the drug by 30% or more, preferably 50% or more, more preferably 60% or more, compared with the ropivacaine hydrochloride injection at the same dose. The pharmaceutical composition has a duration of action of 12 h or more, 24 h or more, or even 48 h or more, for example, 12-24 h, 24-48 h, 12-48 h, etc. The effective therapeutic dose of the composition can be reduced by 10% or more, preferably 20% or more, more preferably 30% or more, compared with conventional sustained-release preparations. When the composition achieves the same analgesic effect as that of the conventional sustained-release preparation, the motor block can be improved by 20%, preferably 30%, and more preferably 60%.

In another aspect, the present invention provides a method of preparing the above-mentioned long-acting ropivacaine pharmaceutical composition, comprising the steps of:

- dispersing the prescribed amount of ropivacaine, the prescribed amount of pharmaceutical oil, the prescribed amount of pharmaceutical phospholipid, the prescribed amount of efficacy enhancer and optionally, the prescribed amount of antioxidant and optionally, the prescribed amount of acid-base regulator, and the prescribed amount of pharmaceutical solvent in an excess volatile organic solvent evenly;
- removing the excess volatile organic solvent, for example by evaporation and/or vacuum pump drying;
- optionally, supplementing the pharmaceutical solvent to the prescribed amount and mixing them well.

In this method, the efficacy enhancer and the acid-base regulator can be added simultaneously or sequentially with ropivacaine, the antioxidant, the pharmaceutical solvent, the pharmaceutical oil, and the pharmaceutical phospholipid, or added in the last step.

In the present invention, examples of the volatile organic solvent include, but are not limited to, ethanol, dichloromethane, chloroform, methanol, and the like.

In another aspect, the present invention provides a method of preparing the above-mentioned long-acting ropivacaine pharmaceutical composition, comprising the steps of:

- adding ropivacaine to a pharmaceutical solvent to fully dissolve the ropivacaine to obtain a ropivacaine solution;
- mixing a pharmaceutical phospholipid and a pharmaceutical oil evenly (under nitrogen protection), adding the ropivacaine solution, and mixing evenly;
- then adding the efficacy enhancer thereto, mixing them evenly, and filtering to give the long-acting ropivacaine pharmaceutical composition.

Optionally, the antioxidant and the acid-base regulator can be added in any step of the above process.

In another aspect, the present invention provides a method of preparing the above-mentioned long-acting ropivacaine pharmaceutical composition, comprising the steps of:

- dissolving ropivacaine in a pharmaceutical solvent to obtain a ropivacaine solution;
- adding a pharmaceutical phospholipid and dissolving evenly;
- adding a pharmaceutical oil and an efficacy enhancer, mixing them evenly and filtering to give the long-acting ropivacaine pharmaceutical composition.

Optionally, the antioxidant and the acid-base regulator can be added in any step of the above process.

In some embodiments, the composition is a clear solution.

According to practical needs, the above methods may also include steps of sub-packaging and optional degermation or sterilization. The degermation is, for example, filtration degermation. The sterilization is, for example, moist heat sterilization.

In another aspect, the present invention provides a use of the above-mentioned long-acting ropivacaine pharmaceutical composition in preparation of a pain relief medicament. The composition can controllably adjust the time for treating pain, and can provide a long-acting analgesic effect. The pain relief medicament can be in the form of various dosage forms or packaged kits for topical administration, for example, suitable for local injection, such as subcutaneous or intramuscular injection administration, or direct instillation at the incision, or incision infiltration, or administration at the nerve plexus, or intra-articular injection, preferably subcutaneous injection, more preferably in the form of a dosage form or a packaged kit for subcutaneous infiltration administration.

In some embodiments, the pain is postoperative pain.

In some embodiments, the pharmaceutical composition provides pain relief for at least about 12 hours. In some embodiments, the pharmaceutical composition provides pain relief between 12 and 24 hours. In some embodiments, the pharmaceutical composition provides pain relief for at least about 24 hours. In some embodiments, the pharmaceutical composition provides pain relief between 24 and 48 hours. In some embodiments, the pharmaceutical composition provides pain relief for at least about 48 hours. In some embodiments, the pharmaceutical composition provides pain relief between 48 and 72 hours. In some embodiments, the pharmaceutical composition provides pain relief for at least about 72 hours.

In some embodiments, the composition has a significant advantage in pain relief time over the composition that is not added with the efficacy enhancer and the composition with an amount of the efficacy enhancer outside the scope of the present invention.

The long-acting ropivacaine pharmaceutical composition provided by the present invention can be administered by local injection, such as subcutaneous or intramuscular injection, or administered by direct instillation at the incision, or administered by incision infiltration, or administered at the nerve plexus, or administered by intra-articular injection, preferably administered by subcutaneous injection, more preferably administered by subcutaneous infiltration.

The expected total daily dose of the long-acting ropivacaine pharmaceutical composition provided by the present invention is 5-1000 mg, preferably 10-500 mg of the active drug.

Terminology Explanation

The term "ropivacaine" refers to a ropivacaine free base or a pharmaceutically acceptable salt of ropivacaine. Here, the ropivacaine free base may be in the form of a solvate of ropivacaine free base. And the pharmaceutically acceptable salt of ropivacaine may be in the form of a solvate of the pharmaceutically acceptable salt of ropivacaine, unless otherwise explained by the context.

The term "sensory nerve block" means that the process in which the nerve endings in any sensory site transmit impulses to the center is blocked, resulting in loss of perception, and can be understood as sensory block. In the present invention, it refers specifically to loss of pain perception. The analgesia in the present invention refers to blockade of sensory nerves, and the efficacy refers to the effect of blockade of sensory nerves.

The term "motor nerve block" means that the process in which nerve fibers send out nerve impulses to the surrounding area and produce movement is blocked, and is manifested as impaired motor function and limited activity, and can be understood as motor block.

The term "effective treatment time" can be understood as the length of time that the drug is effective, and can be understood as the duration of action.

The term "effective therapeutic dose" refers to the dose of the drug required to achieve the unit effective treatment time.

The term "conventional sustained-release formulation" can be understood as a composition having a similar prescription to the present invention without the efficacy enhancer, for example the pro-liposome preparation disclosed in CN104427977B.

The term "composition" may be understood as a pharmaceutical composition, a pharmaceutical prescription, a pharmaceutical recipe, a formulation or a pharmaceutical preparation.

The term "bioavailability" refers to the speed and degree of the drug being absorbed into human body's circulation. It is compared by using the area under the plasma concentration-time curve (AUC) in the present invention.

The term "onset concentration" refers to the minimum plasma concentration at which the drug is effective. Only when the plasma concentration is greater than this value, the drug can be effective. It can be understood as the minimum effective concentration or the lowest effective concentration.

The term "effective bioavailability" refers to the area under the plasma concentration-time curve that is greater than the onset concentration.

The present invention provides a long-acting ropivacaine pharmaceutical composition through creative research. The composition has good solubility for both ropivacaine free base and salts thereof, and has good syringeability for injection and controllable release rate. Compared with the commercially available ropivacaine hydrochloride injection, the composition has a significantly reduced $C_{max}$ and an improved safety. The most critical thing is that the composition of the present invention can prolong the effective treatment time, reduce the effective treatment dose, and can improve the bioavailability and effective bioavailability, so as to ensure that the drug can be fully exposed to avoid the waste of the drug and reduce the potential risk of neurotoxicity, while meeting the demand of clinical analgesic time. The composition of the invention can solve the problems of clinical treatment and safety requirements of local anesthetic preparations, and has a good application prospect.

Compared with the ropivacaine pharmaceutical preparations studied, the present invention has the following advantages:

1. Compared with the commercial ropivacaine hydrochloride injection at the same dose, the present invention can reduce the peak plasma concentration by at least 30%, preferably at least 50%, and more preferably at least 60%, which improves the safety of clinical medication.

2. The pharmaceutical composition of the present invention may have a duration of action of 12 h or more, and preferably 24 h or more, which reduces the number of repeated administrations, increases patient compliance, and reduces treatment cost.

3. Compared with conventional sustained-release preparations, the pharmaceutical composition of the present invention can make the drug release more complete, significantly improve bioavailability and effective bioavailability, avoid long-term retention of ineffective drug, and reduce the risk of nerve fiber damage.

4. Compared with the conventional sustained-release preparation at the same dose, the pharmaceutical composition of the present invention can significantly prolong the action time and reduce the treatment cost.

5. Under the same analgesic effect, the pharmaceutical composition of the present invention can improve motor block, reduce neurotoxicity and facilitate pain recovery, compared with conventional sustained-release preparations.

6. Compared with conventional sustained-release preparations, the pharmaceutical composition of the present invention can reduce the effective therapeutic dose, and can reduce the dosage of the drug under the condition of reaching the same duration of action, improve the utilization of the drug, avoid waste of the drug, and reduce the risk of toxic reactions.

7. The pharmaceutical composition of the present invention has a controllable duration of action, and provides beneficial value of on-demand selection for the development and clinical use of ropivacaine.

8. The pharmaceutical composition of the present invention has small local irritation, and has good biocompatibility and safety.

9. Compared with the local anesthetic preparations studied, the present invention has the advantages of good safety, high bioavailability, controllable sustained-release effect, high drug utilization, low neurotoxicity, and good injection syringeability.

DRAWINGS

MODE FOR CARRYING OUT THE INVENTION

Figure 1:
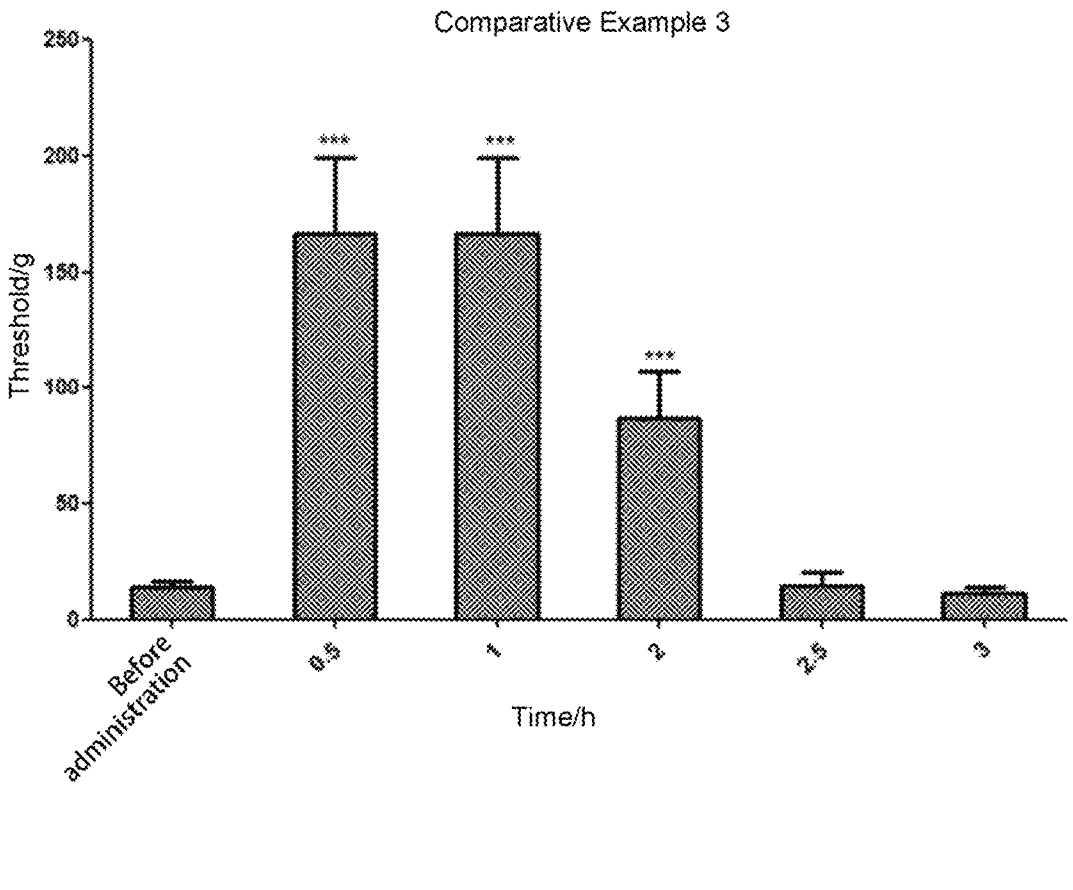
FIG. 1 shows the observation results of paw withdrawal mechanical thresholds of animals in Comparative Example 3.

The composition, preparation method and use of the present invention are further illustrated by providing the following examples and experimental examples, but the present invention is not limited thereto. The present invention is further described in detail below with reference to the examples, but a person skilled in the art should understand that the present invention is not limited to these examples and the used preparation methods. Moreover, a person skilled in the art can make equivalent substitutions, combinations, improvements or modifications to the present invention based on the description of the present invention, and all of them fall within the scope of the present invention.

EXAMPLE

Comparative Examples 1 and 2

According to the formulation listed in Table 1, the pharmaceutical oil and the pharmaceutical solvent were mixed uniformly, and ropivacaine was added. The resulting mixture was vortexed, and ultrasonicated to obtain a turbid and opaque liquid;

The drug ropivacaine was tried to be first dissolved in the pharmaceutical solvent, and the dissolution process was relatively rapid at this time. Then the prescribed amount of pharmaceutical oil was added. The resultant was vortexed and a phenomenon of white turbidity immediately appeared.

TABLE 1

Formulation of Pharmaceutical Composition

| Formulation (w/w) | | Comparative Example 1 | Comparative Example 2 |
|---|---|---|---|
| Drug Ropivacaine | ropivacaine hydrochloride | 2% | 2% |
| Pharmaceutical oil | castor oil | 88% | / |
| | medium chain triglyceride | / | 88% |
| Pharmaceutical solvent | benzyl alcohol | 10% | 10% |
| | | opaque | opaque |

Comparative Example 3: Ropivacaine Hydrochloride Injection

Ropivacaine hydrochloride as the active pharmaceutical ingredient and sodium chloride were weighed in the prescribed amounts, and placed into a vial. Purified water was added. The resultant was vortexed and ultrasonicated to be dissolved to be clear to obtain a uniform solution. The solution was adjusted to pH value=4.0-6.0 to obtain the ropivacaine hydrochloride injection.

TABLE 2

Formulation of Comparative Example 3

| Formulation | Ratio |
|---|---|
| ropivacaine hydrochloride | 10 mg/ml |
| sodium chloride | 7.1 mg/ml |
| purified water | appropriate amount |

Comparative Example 4: Pro-Liposome Preparation of CN104427977B (Conventional Sustained-Release Preparation)

Ropivacaine hydrochloride monohydrate, lecithin PL-90G, castor oil, and cysteine hydrochloride in the prescribed amounts were added to a pre-weighed round bottom flask, and weighed. An excess of anhydrous ethanol was added. The flask was placed in an ultrasonic wave water bath and subjected to ultrosonication to completely disperse the phospholipid and completely dissolve each component, while ensuring that the amount of anhydrous ethanol exceeded the required final amount. At this time, the round bottom flask was connected to a suitable rotary evaporator, and subjected to evaporation under reduced pressure until the weight change of the round bottom flask indicated that the amount of anhydrous ethanol was less than or equal to 6%. The flask was allowed to be cooled to room temperature. If necessary, anhydrous ethanol was again added until it reached 6%. The resultant was mixed well, and the content was transferred to a glass vial, and stored at room temperature.

TABLE 3

Formulation of Comparative Example 4

| Formulation | Ratio (w/w) |
|---|---|
| ropivacaine hydrochloride monohydrate | 4.78% |
| Lecithin PL-90G | 53.91% |
| castor oil | 35.21% |
| anhydrous ethanol | 6.0% |
| cysteine hydrochloride | 0.1% |

Comparative Example 5: Oil Solution Preparation of CN103142458B

Ropivacaine free base was weighed in the prescribed amount, and placed into a vial. Benzyl alcohol and benzyl benzoate were added. The resultant was stirred to dissolve the drug completely. Then soybean oil was added. Then the resultant was stirred evenly to obtain a clear oily solution.

TABLE 4

Formulation of Comparative Example 5

| Formulation | Ratio |
|---|---|
| Ropivacaine free base | 30 mg/ml |
| Soybean oil | 75% (v/v) |
| Benzyl benzoate | 15% (v/v) |
| Benzyl alcohol | 10% (v/v) |

Comparative Example 6: Preparation Provided by CN109316602A

Ropivacaine free base and parecoxib were weighed in the prescribed amounts, and benzyl alcohol, benzyl benzoate and ethanol in the prescribed amounts were added in turn. The resultant was shaken and stirred until the drugs were completely dissolved. Then the lecithin E80 was added in the prescribed amount, and the resultant was shaken and stirred until it was completely dissolved. An appropriate amount of castor oil was added and shaken well. The resultant was placed for 5 h at 2-8° C. and at room temperature, respectively. The obvious needle-like precipitation was observed under both conditions.

TABLE 5

Formulation of Comparative Example 6

| Formulation | Ratio (w/w) |
|---|---|
| Ropivacaine free base | 8% |
| Parecoxib | 3% |
| Lecithin E80 | 26% |
| Benzyl benzoate | 15% |
| Benzyl alcohol | 10% |
| Ethanol | 10% |
| Castor oil | 28% |

Comparative Example 7: Preparation Provided by CN109316602A

Ropivacaine free base and parecoxib were weighed in the prescribed amounts, and benzyl alcohol, benzyl benzoate and ethanol in the prescribed amounts were added in turn. A plug was covered. The resultant was stirred until the drugs were completely dissolved. The egg yolk lecithin PC-98T was then added, and the resultant was shaken and stirred until it was completely dissolved. An appropriate amount of soybean oil was added to the prescribed amount. The resultant was mixed well.

TABLE 6

Formulation of Comparative Example 7

| Formulation | Amount |
|---|---|
| Ropivacaine free base | 3% w/v |
| Parecoxib | 1.5% w/v |
| Ethanol | 10% v/v |
| Benzyl benzoate | 20% v/v |
| Benzyl alcohol | 10% v/v |
| egg yolk lecithin PC-98T | 20% w/v |
| Soybean oil | added to 100% v/v |

Comparative Examples 8 and 9

Ropivacaine hydrochloride, propylene glycol, soybean lecithin S100, castor oil, and meglumine in the prescribed amounts were added to a pre-weighed round bottom flask, and weighed. An excess of anhydrous ethanol was added. The flask was placed in an ultrasonic wave water bath, and subjected to ultrasonication to dissolve each component completely. At this time, the round bottom flask was connected to a suitable rotary evaporator, and subjected to evaporation under reduced pressure until the weight change of the round bottom flask indicated that the anhydrous ethanol had been completely removed. The flask was allowed to be cooled to room temperature. The fish oil was added in the prescribed amount. The resultant was mixed well, and the content was transferred to a glass vial, and stored at room temperature.

TABLE 7

Formulation Information of Comparative Examples 8 and 9

| Formulation | Ratio of Comparative Example 8 (w/w) | Ratio of Comparative Example 9 (w/w) |
|---|---|---|
| Ropivacaine hydrochloride | 4.5% | 4.5% |
| Soya bean lecithin S100 | 42% | 42% |
| Castor oil | 38.2% | 23.2% |
| Propylene glycol | 15% | 15% |
| Fish oil 3322 | / | 15% |
| Meglumine | 0.3% | 0.3% |

Example 1

Preparation of Long-Acting Pharmaceutical Compositions

The preparation process of the compositions in Table 8: a prescribed amount of ropivacaine was added to the pharmaceutical solvent, and the mixture was stirred to dissolve the drug to obtain a drug solution; the pharmaceutical phospholipid was added to the corresponding pharmaceutical oil, and the mixture was subjected to high-speed shearing until the pharmaceutical phospholipid was completely dissolved; the drug solution was added thereto, and the mixture was mixed well, and then the efficacy enhancer was added, and the mixture was stirred to obtain a drug-containing solution, and the solution was filtered and packed, filled with nitrogen, sealed, and then sterilized by moist heat to obtain a clear and transparent liquid.

TABLE 8

Formulation of Pharmaceutical Compositions

| Formulation (w/w) | | Composition 1 | Composition 2 | Composition 3 | Composition 4 | Composition 5 | Composition 6 |
|---|---|---|---|---|---|---|---|
| Drug Ropivacaine | | 2% ropivacaine hydrochloride | 1% ropivacaine hydrochloride | 1% ropivacaine free base | 2% ropivacaine mesylate | 3% ropivacaine hydrochloride | 3.5% ropivacaine free base |
| Pharmaceutical oil | Castor oil | 43% | 57% | 76% | / | 44% | 56.5% |
| | Medium chain triglyceride | / | / | / | 39% | / | / |
| Pharmaceutical phospholipid | Egg yolk lecithin PC-98T | / | / | / | 40% | 32% | / |
| | Soya bean lecithin S100 | 35% | 30% | 10% | / | / | 17% |
| Efficacy enhancer | Fish oil 3322 | 5% | 2% | 5% | / | 4% | 8% |
| | Purple perilla seed oil | / | / | / | 6% | 2% | / |
| Pharmaceutical solvent | Benzyl alcohol | / | / | 8% | 13% | 15% | 15% |
| | Propylene glycol | 15% | 10% | / | / | / | / |
| Phenomenon | | clear and transparent | clear and transparent | clear and transparent | clear and transparent | clear and transparent | clear and transparent |

It can be seen from the results that all the compositions prepared by adding an appropriate amount of pharmaceutical phospholipid were clear and transparent, and the purpose of improving the solubility of the drug in the composition system was achieved.

The preparation process of the compositions in Table 9: a prescribed amount of ropivacaine was added to the pharmaceutical solvent to obtain a drug solution; the pharmaceutical phospholipid was added, and the mixture was stirred until the pharmaceutical phospholipid was completely dissolved; then the pharmaceutical oil and the efficacy enhancer were added, the mixture was stirred to mix well to obtain a drug-containing solution, and the solution was filtered and packed, filled with nitrogen, sealed, and then sterilized by moist heat to obtain a clear and transparent liquid.

The preparation process of the compositions in Table 10: The drug ropivacaine, the pharmaceutical oil, the pharmaceutical phospholipid, the pharmaceutical solvent, and the efficacy enhancer were weighted in the prescribed amounts, and placed into a pre-weighed round bottom flask, and weighed. An excess of anhydrous ethanol was added. Then the flask was placed in an ultrasonic wave water bath, and subjected to ultrasonication to completely disperse phospholipid and completely dissolve each component. At this time, the round bottom flask was connected to a suitable rotary evaporator, and subjected to evaporation under reduced pressure until the weight change of the round bottom flask indicated that the anhydrous ethanol had been completely removed. If necessary, ethanol was supplemented to the prescribed amount, and the mixture was mixed well. The resulting drug solution was filtered, packed, filled with nitrogen, sealed to obtain a clear and transparent liquid.

TABLE 9

Formulation of Pharmaceutical Compositions

| Formulation (w/w) | | Composition 7 | Composition 8 | Composition 9 | Composition 10 |
|---|---|---|---|---|---|
| Drug ropivacaine | Ropivacaine hydrochloride | 4% | 3.5% | 5% | 4% |
| Pharmaceutical oil | Castor oil | 40% | 33.5% | 22% | 28% |
| Pharmaceutical phospholipid | Soya bean lecithin S100 | 38% | 42% | 45% | / |
| | Egg yolk lecithin PC-98T | / | / | / | 45% |
| Efficacy enhancer | Fish oil 3322 | 5% | / | 8% | / |
| | Linseed oil | / | 6% | / | 5% |
| Pharmaceutical solvent | Benzyl alcohol | 13% | 15% | 20% | 15% |
| | Benzyl benzoate | / | / | / | 3% |
| Phenomenon | | clear and transparent | clear and transparent | clear and transparent | clear and transparent |

TABLE 10

| Formulation of Pharmaceutical Compositions | | | | | | | |
|---|---|---|---|---|---|---|---|
| Formulation (w/w) | | Composition 11 | Composition 12 | Composition 13 | Composition 14 | Composition 15 | Composition 16 |
| Drug Ropivacaine | | 5% ropivacaine hydrochloride | 2% ropivacaine hydrochloride | 2% ropivacaine hydrochloride | 3.5% ropivacaine free base | 2.5% ropivacaine mesylate | 3.5% ropivacaine hydrochloride |
| Pharmaceutical oil | Sesame oil | / | 54% | / | / | / | / |
| | Castor oil | 34% | / | / | 59.5% | / | 45.5% |
| | Soybean oil | / | / | / | / | 42.5% | / |
| | Medium chain triglyceride | / | / | 38% | / | / | / |
| Pharmaceutical phospholipid | Soya bean lecithin S100 | 40% | / | / | 15% | 35% | 35% |
| | Egg yolk lecithin PC-98T | / | 32% | 50% | / | / | / |
| Efficacy enhancer | Fish oil 3322 | / | 2% | 4% | / | / | / |
| | Laver oil | 2% | / | / | 2% | / | / |
| | Linseed oil | / | / | / | / | / | 6% |
| | Purple perilla seed oil | / | / | / | / | 5% | / |
| Solvent | Benzyl alcohol | 19% | 2% | 6% | 15% | 10% | 10% |
| | Ethanol | / | 8% | / | / | 5% | / |
| | Benzyl benzoate | / | / | / | 5% | / | / |
| Phenomenon | | clear and transparent | clear and transparent | clear and transparent | clear and transparent | clear and transparent | clear and transparent |

The preparation process of the compositions in Table 11: The drug ropivacaine, the pharmaceutical oil, the pharmaceutical phospholipid, the pharmaceutical solvent, the antioxidant, the efficacy enhancer and the acid-base regulator were weighted in the prescribed amounts, and placed into a pre-weighed round bottom flask, and weighed. An excess of anhydrous ethanol was added. Then the flask was placed in an ultrasonic wave water bath, and subjected to ultrasonication to completely disperse the phospholipid and completely dissolve each component. At this time, the round bottom flask was connected to a suitable rotary evaporator, and subjected to evaporation under reduced pressure until the weight change of the round bottom flask indicated that the anhydrous ethanol had been completely removed. The resulting drug solution was filtered, packed, filled with nitrogen, sealed, and then sterilized by moist heat to obtain a clear and transparent liquid.

TABLE 11

| Formulation of Pharmaceutical Compositions | | | | | | | |
|---|---|---|---|---|---|---|---|
| Formulation (w/w) | | Composition 17 | Composition 18 | Composition 19 | Composition 20 | Composition 21 | Composition 22 |
| Drug Ropivacaine | | 4.5% ropivacaine hydrochloride | 3% ropivacaine hydrochloride | 6% ropivacaine hydrochloride | 3.5% ropivacaine hydrochloride | 7% ropivacaine hydrochloride | 4.5% ropivacaine hydrochloride |
| Pharmaceutical oil | Sesame oil | / | 47.8% | / | / | / | / |
| | Castor oil | 29% | / | 17.6% | 44% | 15% | 30% |
| Pharmaceutical phospholipid | Soya bean lecithin S100 | / | 35% | 50% | 30% | 52% | 35% |
| | Egg yolk lecithin PC-98T | 43% | / | / | / | / | / |
| Efficacy enhancer | Fish oil 3322 | 5% | / | 6% | / | 1% | 8% |
| | Linseed oil | / | 2% | / | 2% | / | / |
| Solvent | Propylene glycol | 18% | / | / | 15% | / | 21.7% |
| | Benzyl alcohol | / | 12% | 20% | 5% | 22.5% | / |
| Antioxidant | α-tocopherol | / | / | / | / | 0.4% | / |
| | L-ascorbyl palmitate | / | / | 0.2% | / | 0.1% | / |
| | α-tocopheryl acetate | / | / | / | 0.1% | / | / |
| Acid-base regulator | Meglumine | 0.5% | 0.2% | / | / | / | 0.8% |
| | Diethanolamine | / | / | / | 0.4% | 2% | / |
| | Ethylenediamine | / | / | 0.2% | / | / | / |
| Phenomenon | | clear and transparent | clear and transparent | clear and transparent | clear and transparent | clear and transparent | clear and transparent |

The preparation process of the compositions in Table 12: The drug ropivacaine, the pharmaceutical oil, the pharmaceutical phospholipid, the pharmaceutical solvent, the efficacy enhancer and the acid-base regulator were weighted in the prescribed amounts, and placed into a pre-weighed round bottom flask, and weighed. An excess of anhydrous ethanol was added. Then the flask was placed in an ultrasonic wave water bath, and subjected to ultrasonication to completely disperse the phospholipid and completely dissolve each component. At this time, the round bottom flask was connected to a suitable rotary evaporator, and subjected to evaporation under reduced pressure until the weight change of the round bottom flask indicated that the anhydrous ethanol had been completely removed. The resulting drug solution was filtered, packed, filled with nitrogen, sealed, and then sterilized by moist heat to obtain a clear and transparent liquid.

TABLE 12

Formulation of Pharmaceutical Compositions

| Formulation (w/w) | Composition 23 | Composition 24 | Composition 25 |
|---|---|---|---|
| Drug Ropivacaine | 4.5% ropivacaine hydrochloride | 4.5% ropivacaine hydrochloride | 4.5% ropivacaine hydrochloride |
| Pharmaceutical oil | 33.2% castor oil | 33.2% castor oil | 33.2% castor oil |
| Pharmaceutical phospholipid | 42% soya bean lecithin S100 | 42% soya bean lecithin S100 | 42% soya bean lecithin S100 |
| Efficacy enhancer | 5% fish oil 3322 | 5% fish oil 1812 | 5% algal oil |
| Solvent | 15% propylene glycol | 15% propylene glycol | 15% propylene glycol |
| Acid-base regulator | 0.3% meglumine | 0.3% meglumine | 0.3% meglumine |
| Phenomenon | clear and transparent | clear and transparent | clear and transparent |

EXPERIMENTAL EXAMPLE

Experimental Example 1 Stability Investigation

The pharmaceutical compositions prepared in Example 1 were placed to observe the appearance to determine its stability. If there was no visible precipitate, it could be considered that the composition had good storage stability.

TABLE 13

Stability Investigation Result of Pharmaceutical Compositions

| Composition No. | Appearance | Appearance stability after placed for one month |
|---|---|---|
| Comparative Example1 | turbid and opaque | / |
| Comparative Example2 | turbid and opaque | / |
| Composition 3 | clear and transparent | no significant change |
| Composition 4 | clear and transparent | no significant change |
| Composition 5 | clear and transparent | no significant change |
| Composition 6 | clear and transparent | no significant change |
| Composition 7 | clear and transparent | no significant change |
| Composition 8 | clear and transparent | no significant change |
| Composition 9 | clear and transparent | no significant change |
| Composition 10 | clear and transparent | no significant change |
| Composition 11 | clear and transparent | no significant change |
| Composition 12 | clear and transparent | no significant change |
| Composition 13 | clear and transparent | no significant change |

TABLE 13-continued

Stability Investigation Result of Pharmaceutical Compositions

| Composition No. | Appearance | Appearance stability after placed for one month |
|---|---|---|
| Composition 14 | clear and transparent | no significant change |
| Composition 15 | clear and transparent | no significant change |
| Composition 16 | clear and transparent | no significant change |
| Composition 17 | clear and transparent | no significant change |
| Composition 22 | clear and transparent | no significant change |
| Composition 23 | clear and transparent | no significant change |
| Composition 24 | clear and transparent | no significant change |

It can be seen from the results that the prepared compositions were all clear and transparent, indicating that they had good storage stability. However, the preparation provided by CN109316602A (i.e., Comparative Example 6) had obvious precipitation after being placed for 5 hours, showing poor stability.

Some of the compositions were selected, placed under corresponding conditions, and detected for their changes in the content and the total amount of related substance according to the following methods.

Testing Equipment:

High performance liquid chromatograph 1260, Agilent Technologies Co., Ltd., USA.

Detection Conditions:

Chromatographic column: octadecylsilane-bonded silica gel column (4.6 mm×150 mm, 5 μm, Agilent Technologies Co., Ltd., USA); the mobile phase: a solution of acetonitrile-disodium hydrogen phosphate buffer (adjusted to pH=8.0 by phosphoric acid), the flow rate: 1 ml/min, the column temperature: 30° C., and the detection wavelength: 240 nm.

Preparation Method:

Test sample solution: an appropriate amount of the test sample was precisely weighed and placed into a volumetric flask. Methanol was added to dissolve the test sample, and the volume was set to the scale line. The mixture was vortexed and ultrasonicated to obtain the test sample solution.

Content reference substance solution: An appropriate amount of ropivacaine drug reference substance was weighed, placed into a volumetric flask, and precisely weighed. Methanol was used to dissolve the ropivacaine drug reference substance, and the volume was set to the scale line to obtain the content reference substance solution.

Related substance reference solution: 1 ml of the test sample solution was precisely pipetted into a 100 ml volumetric flask, and methanol was added to dilute to the scale line to obtain the related substance reference solution.

The above solution was precisely taken and injected into a liquid chromatograph. The external standard method was used to calculate the content. The self-dilution control method was used to calculate the related substance. The total amount of the related substance was calculated. The results were shown in Table 14.

TABLE 14

Determination result of the content and related substance of the compositions

| Composition | Content % | | | | | Total amount of related substance % | | | | |
|---|---|---|---|---|---|---|---|---|---|---|
| | Day 0 | 3 months under acceleration condition | 6 months under acceleration condition | 3 months under acceleration condition | 6 months under acceleration condition | Day 0 | 3 months under acceleration condition | 6 months under acceleration condition | 3 months under acceleration condition | 6 months under acceleration condition |
| Composition 3 | 98.12 | 99.32 | 98.34 | 98.76 | 99.09 | 0.11 | 0.12 | 0.12 | 0.13 | 0.14 |
| Composition 4 | 101.45 | 100.98 | 101.34 | 100.32 | 99.96 | 0.13 | 0.14 | 0.15 | 0.14 | 0.14 |
| Composition 5 | 99.66 | 99.87 | 100.32 | 99.95 | 98.08 | 0.11 | 0.12 | 0.13 | 0.12 | 0.12 |
| Composition 6 | 98.54 | 98.35 | 97.67 | 97.89 | 98.33 | 0.11 | 0.12 | 0.13 | 0.13 | 0.14 |
| Composition 7 | 100.87 | 100.39 | 99.87 | 99.65 | 99.03 | 0.11 | 0.12 | 0.13 | 0.13 | 0.13 |
| Composition 8 | 99.42 | 98.59 | 98.12 | 100.09 | 98.80 | 0.13 | 0.14 | 0.15 | 0.14 | 0.14 |
| Composition 9 | 101.83 | 101.29 | 100.69 | 99.97 | 100.05 | 0.12 | 0.13 | 0.13 | 0.12 | 0.14 |
| Composition 14 | 101.08 | 100.65 | 100.75 | 101.01 | 100.69 | 0.12 | 0.13 | 0.12 | 0.13 | 0.14 |
| Composition 16 | 99.13 | 98.92 | 99.02 | 98.55 | 98.13 | 0.13 | 0.12 | 0.13 | 0.14 | 0.13 |
| Composition 17 | 99.56 | 100.02 | 99.72 | 99.49 | 100.59 | 0.12 | 0.13 | 0.12 | 0.13 | 0.13 |
| Composition 22 | 100.07 | 99.42 | 100.34 | 99.31 | 99.05 | 0.13 | 0.14 | 0.13 | 0.13 | 0.14 |
| Composition 23 | 100.12 | 100.03 | 99.91 | 99.87 | 100.11 | 0.14 | 0.13 | 0.14 | 0.15 | 0.13 |
| Composition 24 | 99.08 | 99.82 | 100.04 | 99.29 | 99.56 | 0.13 | 0.14 | 0.13 | 0.15 | 0.12 |

It can be seen from the results that the content and related substance of the compositions of the present invention did not change significantly after being placed under accelerated and long-term conditions for 6 months.

It can be seen from the above research results that the compositions of the present invention had good stability.

Experimental Example 2 Syringeability Determination of Pharmaceutical Compositions A 21G needle was used to measure the syringeability of the compositions, and the determination results were shown in Table 15.

TABLE 15

Viscometry results of pharmaceutical compositions

| Composition | Injection syringeability |
|---|---|
| Composition 3 to Composition 25 | They had moderate viscosity, and could pass 21G needle smoothly. |
| Comparative Example 4 | It was difficult to pass 21G needle, and had high viscosity and poor injection syringeability. |
| Comparative Example 5 | It had a low viscosity, and could pass 21G needle smoothly. |

It can be seen from the results that the compositions of the present invention had suitable injection syringeability; while the injection of Comparative Example 4 was difficult, and the injection syringeability was extremely poor.

Experimental Example 3

In the following experimental descriptions, the administration dose referred to the dose calculated according to the amount of hydrochloride of the active ingredient in the preparation (i.e., in the case of free base, converted to hydrochloride).

In Vivo Pharmacodynamic Investigation of Long-Acting Pharmaceutical Compositions (1)

Experimental animals: Male SD rats with 200-300 g were adaptively reared for 3 days, and the base threshold was measured every day.

Experimental grouping and administration dosage: Animals were randomly grouped according to the base threshold, with 6 animals in each group. The different compositions (or the compositions of the comparative examples) were respectively injected into the subcutaneous tissue of voix pedis in rats (the administration volume ranged from 0.10 to 0.35 ml). Pain threshold was measured by von Frey filament pain threshold detector. And motor block was investigated.

The doses administered in the pharmacodynamic test were seen in Table 16.

TABLE 16

Dosing information for in vivo pharmacodynamic studies of pharmaceutical compositions

| Composition | Dose/mg/kg |
|---|---|
| saline placebo | / |
| Comparative example 3 | 13*[1] |
| Comparative example 4 | 45 |

TABLE 16-continued

| Dosing information for in vivo pharmacodynamic studies of pharmaceutical compositions | |
|---|---|
| Composition | Dose/mg/kg |
| Composition 6 | 45 |
| Composition 7 | 45 |
| Composition 9 | 45 |
| Composition 16 | 45 |
| Composition 17 | 45 |
| Composition 22 | 45 |

*[1]In performing the pharmacodynamic test of the present invention, the dose of Comparative Example 3 was tried to be set higher, and it was found that the rats immediately experienced convulsion and tics after injected with 15 mg/kg of Comparative Example 3, and then died. The direct cause of this phenomenon was the toxic reaction that occurred when the plasma concentration was too high. However, for the compositions of the present invention, the rats did not appear the toxic reaction, indicating that the compositions of the present invention have improved safety compared with Comparative Example 3.

Sensory Nerve Block:

Detection method, von Frey acupuncture-foot-lifting method: The rat moved freely in the cage, and the activity space was fixed. After the rat was quiet, the rat's paw was stimulated with von Frey filaments to determine the rat's mechanical paw withdrawal threshold. The higher the mechanical paw withdrawal threshold was, the better the effect of sensory nerve block was.

Evaluation method: Paired t test was used to compare the mechanical paw withdrawal threshold of each group of animals with that before administration, and unpaired t test was used to compare the mechanical paw withdrawal threshold of each group of animals with Comparative Example 4, $P<0.05$ indicated a statistical difference, $P<0.01$ and $P<0.001$ indicated a significant statistical difference.

Measurement time: Since the sensory nerve block of Comparative Example 3 was found to be maintained for a short time during the experiment, up to about 3 hours, the measurement time of Comparative Example 3 was 0.5 h, 1 h, 2 h, 2.5 h, 3 h. However, if the measurement time of the long-acting composition was set according to this setting, the time points would be too dense, which could affect the behavior of rats. Therefore, the time point setting of the long-acting composition was sparser than that of Comparative Example 3. The results were shown in FIGS. 1-3.

Figure 2:
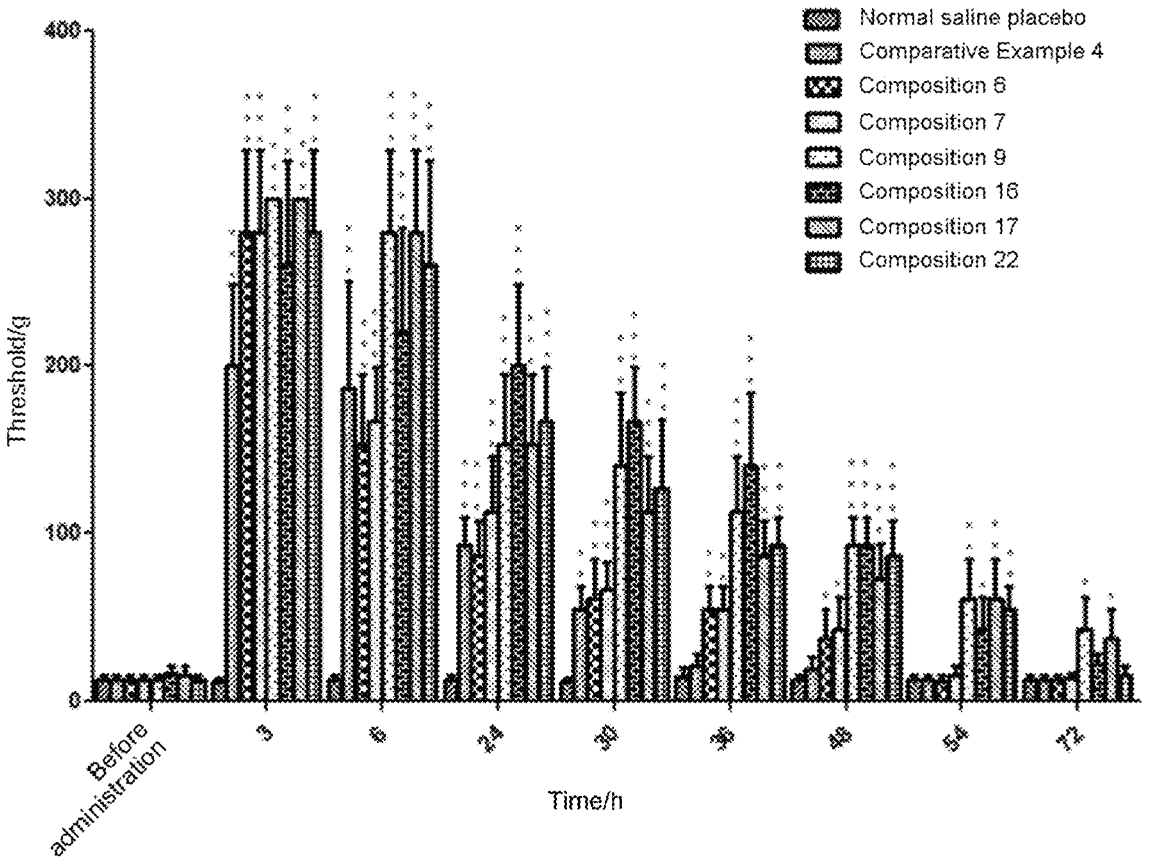
FIG. 2 shows the comparison of the observation results of paw withdrawal mechanical thresholds of Comparative Example 4 and the ropivacaine pharmaceutical compositions (Compositions 6, 7, 9, 16, 17 and 22); *$P<0.001$, $P<0.01$, *$P<0.05$ compared with the paw withdrawal mechanical threshold of each group of animals before administration.

FIGS. 1-2 showed that, compared with the mechanical paw withdrawal threshold before administration, the duration of sensory nerve block in rats of Comparative Examples 3 and 4 was 2 h and about 30 h, respectively. The sensory nerve blocks of Compositions 6, 7, 9, 16, 17 and 22 of the present invention were maintained for 48 h, 48 h, 72 h, 54 h, 72 h and 54 h, respectively. It can be seen that, at the same dose, the compositions of the present invention can prolong the duration of sensory block by at least 60% compared with Comparative Example 4.

Figure 3:
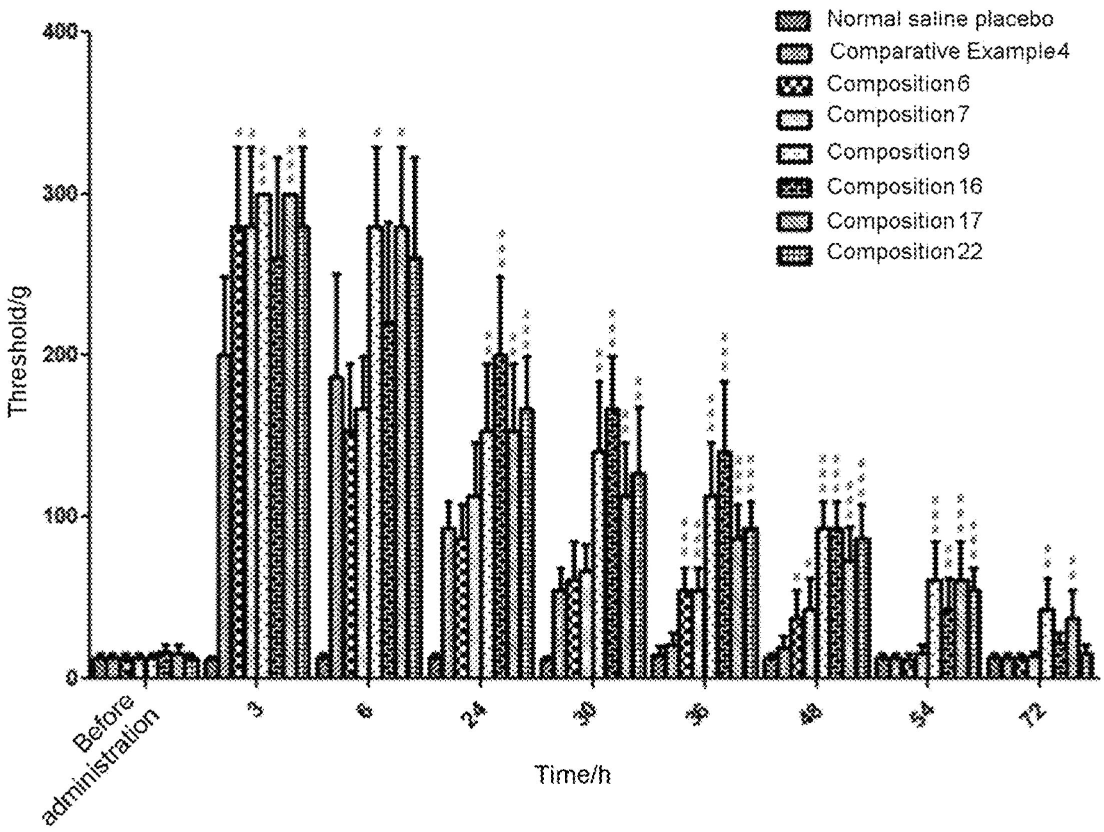
FIG. 3 shows the comparison of the observation results of paw withdrawal mechanical thresholds of Comparative Example 4 and the ropivacaine pharmaceutical compositions (Compositions 6, 7, 9, 16, 17 and 22); ###$P<0.001$, ##$P<0.01$, #$P<0.05$ compared with the paw withdrawal mechanical threshold of Comparative Example 4.

FIG. 3 showed that, compared with Comparative Example 4, all the mechanical paw withdrawal thresholds of Composition 6 in 36-48 h, Composition 7 in 36-48 h, Composition 9 in 36-72 h, Composition 16 in 36-54 h, Composition 17 in 36-72 h, and Composition 22 in 36-54 h had significant differences, indicating that the compositions of the present invention had a significant increase in the efficacy intensity compared with Comparative Example 4, and that the duration of action of the compositions had a significant advantage over Comparative Example 4.

According to the duration of sensory nerve block of the compositions, the effective therapeutic dose of each composition was calculated, and the results were shown in Table 17.

TABLE 17

| Effective therapeutic dose calculation for drug | | | | | | | | |
|---|---|---|---|---|---|---|---|---|
| Parameter | Comparative Example3 | Comparative Example4 | Composition 6 | Composition 7 | Composition 9 | Composition 16 | Composition 17 | Composition 22 |
| R | 6.5 | 1.5 | 0.9 | 0.9 | 0.6 | 0.8 | 0.6 | 0.8 |

Remarks: $R=A/T_t$, wherein A is the administration dose of ropivacaine, $T_t$ is the effective treatment time of the drug in the body, and R is the effective therapeutic dose.

It can be seen that the effective therapeutic dose R of Compositions 6, 7, 9, 16, 17 and 22 can be reduced by at least 40% compared with Comparative Examples 3 and 4, indicating that when the same effective treatment time was achieved, there was a smaller drug dose consumed for the compositions of the present invention, which can avoid the waste of drug and the toxic reactions caused by excess drug in clinic. In addition, the pharmaceutical compositions of the present invention had a controllable pain relief time, which provided the beneficial value of on-demand selection for drug development.

Motor Nerve Block:

While the sensory nerve block was measured, the four-level scoring method was used to evaluate the motor nerve block of the rats in each group. The higher the score was, the more severe the motor block was.

Grade 1 (representing no motor block, expressed as a value of 1): the rat's paw can normally land on the ground, and the weight bearing was normal, and there was no weakness; Grade 2 (representing a slight motor block, expressed as a value of 2): the rat's paw can land normally, but there was slight weakness;

Grade 3 (representing complete motor block, expressed as a value of 3): the rat's paw occasionally touched the ground and there was weakness;

Grade 4 (representing complete motor block, expressed as a value of 4): The rat's paw did not touch the ground at all and there was severe weakness.

Figure 4:
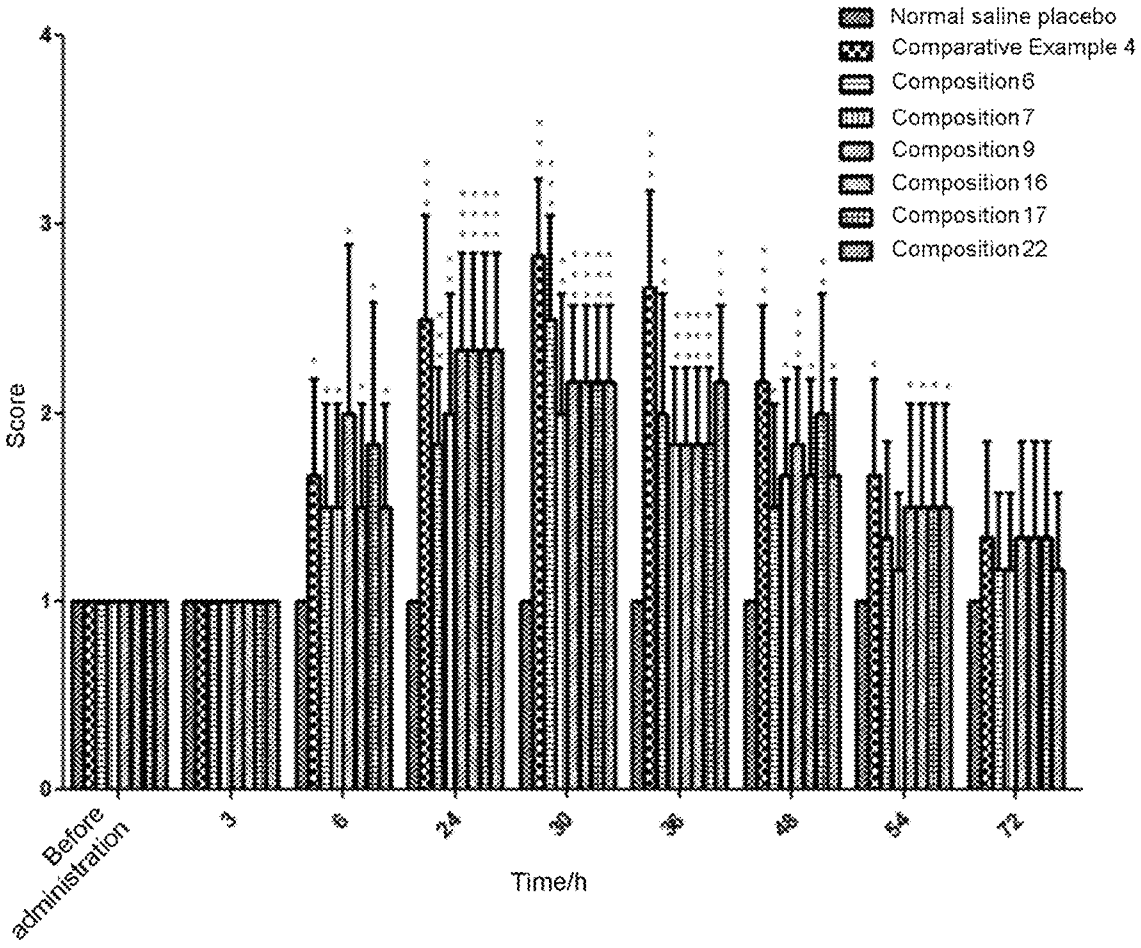
FIG. 4 shows the comparison of the observation results of nerve block scores of saline placebo, Comparative Example 4 and the ropivacaine compositions (Compositions 6, 7, 9, 16, 17 and 22); *$P<0.001$, $P<0.01$, *$P<0.05$ compared with the block score of the saline placebo group.

Evaluation method: Unpaired t test was used to compare the motor nerve block score of each group of animals with that of the normal saline placebo group. $P<0.05$ indicated a statistical difference, and $P<0.01$ and $P<0.001$ indicated a significant statistical difference. The results were shown in FIG. 4.

The duration comparison of motor block and sensory block was shown in Table 18.

TABLE 18

Comparison result of sensory block and motor block for the composition

| Composition | Motor block duration/sensory nerve block duration |
|---|---|
| Comparative Example4 | 1.60 |
| Composition 6 | 1.17 |
| Composition 7 | 0.88 |
| Composition 9 | 0.67 |
| Composition 16 | 0.89 |
| Composition 17 | 0.67 |
| Composition 22 | 0.89 |

Based on the results of the ratio of the motor nerve block duration/sensory nerve block duration of the composition, it can be seen that the motor block duration of the compositions was at least 20% shorter than that of Comparative Example 4 if the same sensory nerve block duration was achieved. It can be seen that the compositions of the present invention had improved motor nerve block condition compared with Comparative Example 4, which meant that the compositions of the present invention did not increase the risk of nerve damage and had higher safety while meeting the clinical analgesic requirements.

In Vivo Pharmacodynamic Investigation of Long-Acting Pharmaceutical Compositions (2)

Figure 5:
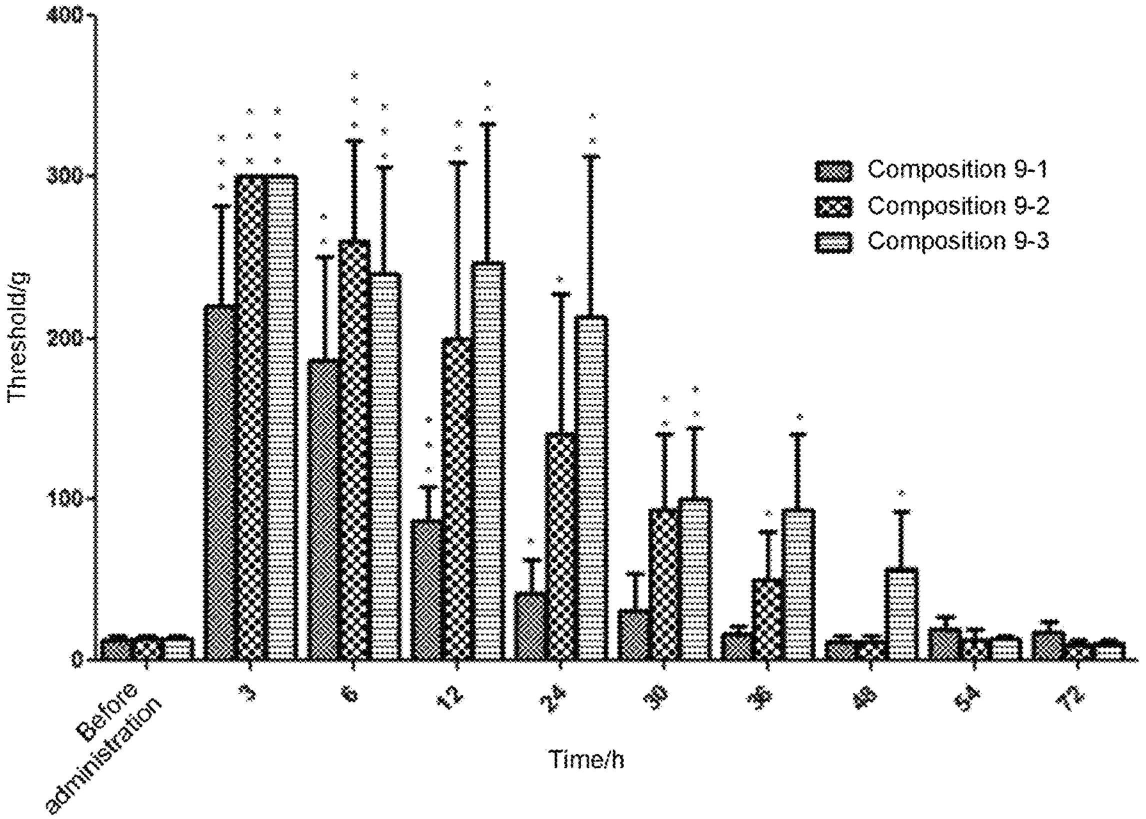
FIG. 5 shows the comparison of the observation results of paw withdrawal mechanical thresholds of the ropivacaine pharmaceutical compositions of the present invention (Compositions 9-1, 9-2 and 9-3); *$P<0.001$, $P<0.01$, *$P<0.05$ compared with the paw withdrawal mechanical threshold of each group of animals before administration.

On the basis of Composition 9, the drug concentration and dosage were changed, and the method of pharmacodynamic investigation (1) was used to determine the sensory nerve block of the corresponding compositions. The compositions and dosing information were shown in Table 19, and the results of sensory nerve block were shown in FIG. 5.

TABLE 19

Formulation and Dosing Information of Compositions

| Composition | Composition (w/w) | Dose mg/kg |
|---|---|---|
| Composition 9-1 | 1.35% ropivacaine hydrochloride + 20% benzyl alcohol + 25.65% castor oil + 45% soybean phospholipid S100 + 8% fish oil 3322 | 15 |
| Composition 9-2 | 2.25% ropivacaine hydrochloride + 20% benzyl alcohol + 24.75% castor oil + 45% soybean phospholipid S100 + 8% fish oil 3322 | 25 |
| Composition 9-3 | 3.15% ropivacaine hydrochloride + 20% benzyl alcohol + 23.85% castor oil + 45% soybean phospholipid S100 + 8% fish oil 3322 | 35 |

The duration of sensory block of Compositions 9-1, 9-2 and 9-3 in vivo was 24 h, 36 h and 48 h, respectively. It can be seen that different pharmaceutical doses can achieve different pain relief time, which provided convenience for clinical on-demand selection.

After calculation, the effective therapeutic doses R of Compositions 9-1, 9-2 and 9-3 were 0.6, 0.7 and 0.7, respectively, which were significantly lower than that of the conventional sustained-release preparation of Comparative Example 4, indicating that the composition of the present invention improved the drug utilization.

In Vivo Pharmacodynamic Investigation of Long-Acting Pharmaceutical Compositions (3)

The ratio and type of the efficacy enhancer in the composition were changed, and the method of pharmacodynamic investigation (1) was used to determine the sensory nerve block of the corresponding composition in animals. The compositions and dosing information were shown in Table 20, and the results of sensory nerve block were shown in FIG. 6 and Table 21.

TABLE 20

Formulation and Dosing Information of Composition

| Composition | Dose mg/kg |
|---|---|
| Comparative example 8 | 45 |
| Comparative example 9 | 45 |
| Composition 23 | 45 |
| Composition 24 | 45 |
| Composition 25 | 45 |

Figure 6:
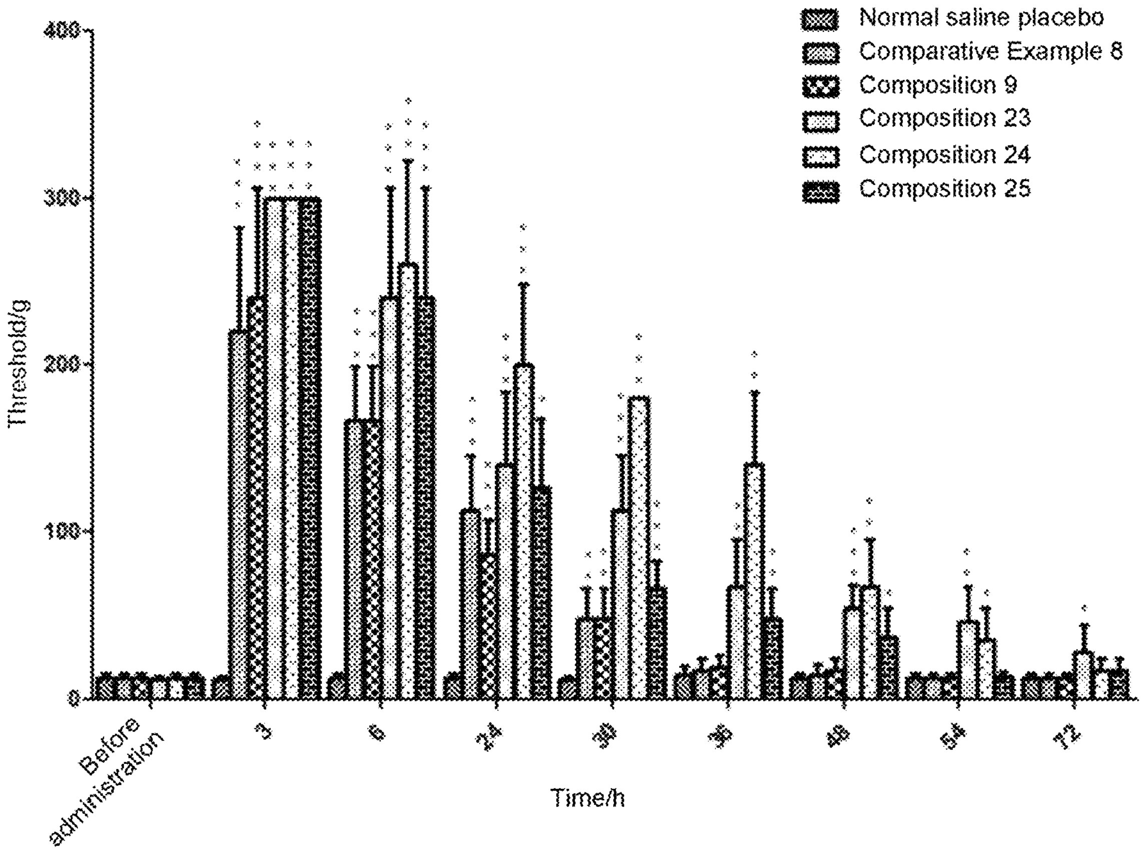
FIG. 6 shows the comparison of the observation results of paw withdrawal mechanical thresholds of animals of Comparative Examples 8, 9 and ropivacaine pharmaceutical compositions (Compositions 23, 24 and 25); *P<0.001, P<0.01, *P<0.05 compared with the paw withdrawal mechanical threshold of each group of animals before administration.

FIG. 6 showed that the durations of sensory nerve block in rats of Comparative Examples 8, 9 and Compositions 23, 24, 25 were 30 h, 30 h, 72 h, 54 h and 48 h, respectively. It can be seen that, at the same dose, the durations of sensory nerve block of Compositions 23-25 (containing 5% efficacy enhancer) were at least 60% longer than those of Comparative Example 8 (without efficacy enhancer) and Comparative Example 9 (containing 15% efficacy enhancer). The contents of eicosapentaenoic acid and docosahexaenoic acid in fish oil 3322 were about 33% and about 22%, respectively, and the contents of eicosapentaenoic acid and docosahexaenoic acid in fish oil 1812 were about 18% and about 12%, respectively. The content of docosahexaenoic acid in the algal oil was about 35%, and there was no eicosapentaenoic acid in the algal oil. The durations of sensory nerve block of Compositions 23, 24 and 25 became shorter sequentially under the same ratio of efficacy enhancer, indicating that the content of eicosapentaenoic acid and docosahexaenoic acid in the composition would have an impact on the duration of action, and that the composition containing both of the fatty acids, eicosapentaenoic acid and docosahexaenoic acid, had more preferable pharmacodynamic results.

TABLE 21

Mechanical Threshold Results for Compositions

| Time/h | Composition 23 | Composition 24 | Composition 25 |
|---|---|---|---|
| Before administration | 12 ± 3 | 13 ± 3 | 13 ± 3 |
| 3 | 300 ± 0#& | 300 ± 0#& | 300 ± 0#& |
| 6 | 240 ± 66# | 260 ± 42# | 240 ± 66# |
| 24 | 153 ± 41#&& | 200 ± 49###&&& | 127 ± 41 |
| 30 | 113 ± 33##&& | 180 ± 0###&&& | 67 ± 16# |
| 36 | 68 ± 28##&& | 140 ± 44###&&& | 49 ± 18##&& |
| 48 | 54 ± 14###&&& | 68 ± 28##&& | 37 ± 18& |

TABLE 21-continued

| Mechanical Threshold Results for Compositions | | | |
|---|---|---|---|
| Time/h | Composition 23 | Composition 24 | Composition 25 |
| 54 | 47 ± 21##&& | 36 ± 19#& | 14 ± 2 |
| 72 | 30 ± 15#& | 18 ± 7 | 18 ± 7 |

Remarks:
#p < 0.05,
p < 0.01,
p < 0.001 v.s. Comparative Example 8;
&p < 0.05,
&&p < 0.01,
&&&p < 0.001 v.s. Comparative Example 9

It can be seen from the results in Table 21 that, compared with Comparative Examples 8 and 9, the mechanical paw retraction thresholds of Compositions 23 to 25 at 24 h or at different time points after 24 h had significant differences, indicating that the duration of action of the compositions had a significant advantage over those of Comparative Examples 8 and 9. It can be seen that the efficacy enhancer achieved an unexpected effect through a certain mechanism.

According to the sensory nerve block duration of the composition, the effective therapeutic dose of each composition was calculated, and the results were shown in Table 22.

TABLE 22

| Effective therapeutic dose calculations for drugs | | | | | |
|---|---|---|---|---|---|
| Parameter | Comparative Example8 | Comparative Example9 | Composition 23 | Composition 24 | Composition 25 |
| R | 1.5 | 1.5 | 0.6 | 0.8 | 0.9 |

Remarks: $R = A/T_t$, wherein A was the administration dose of ropivacaine, $T_t$ was the effective treatment time of the drug in the body, and R was the effective therapeutic dose.

It can be seen that the effective therapeutic dose of the compositions of the present invention was at least 40% lower than those of Comparative Examples 8 and 9, indicating that the compositions of the present invention can improve drug utilization.

Experimental Example 4

In the following experimental descriptions, the administered dose referred to the dose calculated according to the amount of hydrochloride of the active ingredient in the preparation (i.e., in the case of using free base, converted to hydrochloride).

In Vivo Pharmacokinetic Investigation of Long-Acting Pharmaceutical Compositions The obtained pharmaceutical composition was subcutaneously injected into male SD rats. Blood was collected at predetermined time points. The content of the drug in plasma was determined by LC-MS method, and the pharmacokinetics in vivo was investigated.

Experimental animals: male SD rats with a weight of 200-300 g, source: SHANGHAI INSTITUTE OF MATERIA MEDICA, CHINESE ACADEMY OF SCIENCES;

Experimental grouping: Rats were randomly divided into groups according to the following table, with 6 rats in each group;

Administration formulations and dosing information are provided in Table 23.

TABLE 23

| Dosing information for in vivo pharmacokinetic experiments of pharmaceutical compositions | |
|---|---|
| Composition | Dose/mg/kg |
| Comparative example 3 | 13 |
| Comparative example 4 | 45 |

TABLE 23-continued

| Dosing information for in vivo pharmacokinetic experiments of pharmaceutical compositions | |
|---|---|
| Composition | Dose/mg/kg |
| Composition 7 | 45 |
| Composition 9 | 45 |
| Composition 17 | 45 |

Experimental procedure: Rats were subcutaneously injected, and at a predetermined time point, 0.5 ml of blood was collected from the orbit of the rat and placed in a centrifuge tube with heparin sodium anticoagulation. The tube was centrifuged at 3000 rpm for 10 min to separate the plasma, and the plasma concentration was detected by LC-MS method.

The pharmacokinetic (PK) parameters of the compositions were calculated, and the results were statistically analyzed by t-test. The results were shown in Table 24 and FIGS. 7-8.

TABLE 24

PK Parameters of Pharmaceutical Compositions

| Pk parameters | Comparative example 3 | Comparative example 4 | Composition 7 | Composition 9 | Composition 17 |
|---|---|---|---|---|---|
| $C_{max}$(ng/ml) | 365.00 ± 91.73 | 283.38 ± 28.61 | 272.00 ± 29.10 | 209.82 ± 9.70 | 232.70 ± 15.49 |
| AUC(h*ng/ml) | 2332.60 ± 57.98 | 5164.67 ± 344.53 | 5755.06 ± 64.46** | 6218.84 ± 395.54*** | 6568.94 ± 235.99*** |
| $AUC_t$(h*ng/ml) | / | 4596.10 ± 110.34 | 5473.10 ± 153.89*** | 6141.06 ± 163.89*** | 6485.61 ± 232.89*** |

Remarks: AUC was bioavailability, and $AUC_t$ was effective bioavailability.
Remarks:
*p < 0.05
**p < 0.01
***P < 0.001 v.s. Comparative Example 4.

It can be seen from the results in Table 24 that the $C_{max}$ of Compositions 7, 9 and 17 was at least 70% lower than that of Comparative Example 3 at the same dose, and compared with Comparative Example 4, the bioavailability and effective bioavailability of Compositions 7 and 9 were significantly improved.

Figure 9:
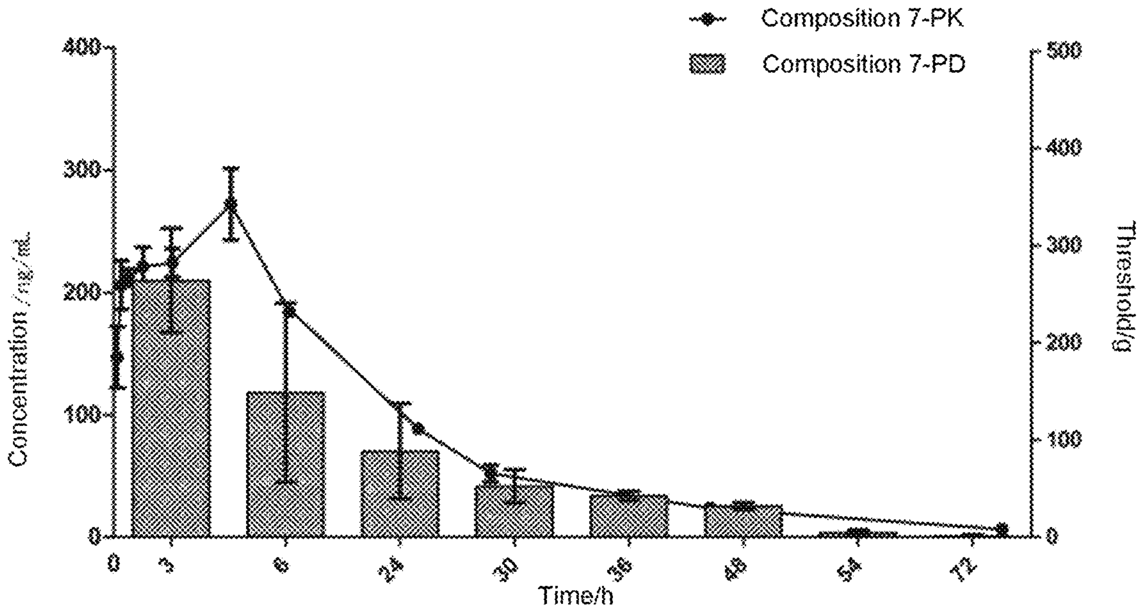
FIG. 9 shows the relationship between the pharmacodynamic effect and pharmacokinetics of the ropivacaine pharmaceutical composition 7 of the present invention.

Combined with the results of the drug pharmacodynamic investigation and the PK curve, FIG. 9 was obtained by fitting and plotting, which showed that the in vivo plasma concentration and drug efficacy of the composition of the present invention were well correlated, indicating that the composition of the present invention had a strong controllability in drug research and clinical use.

Figure 7:
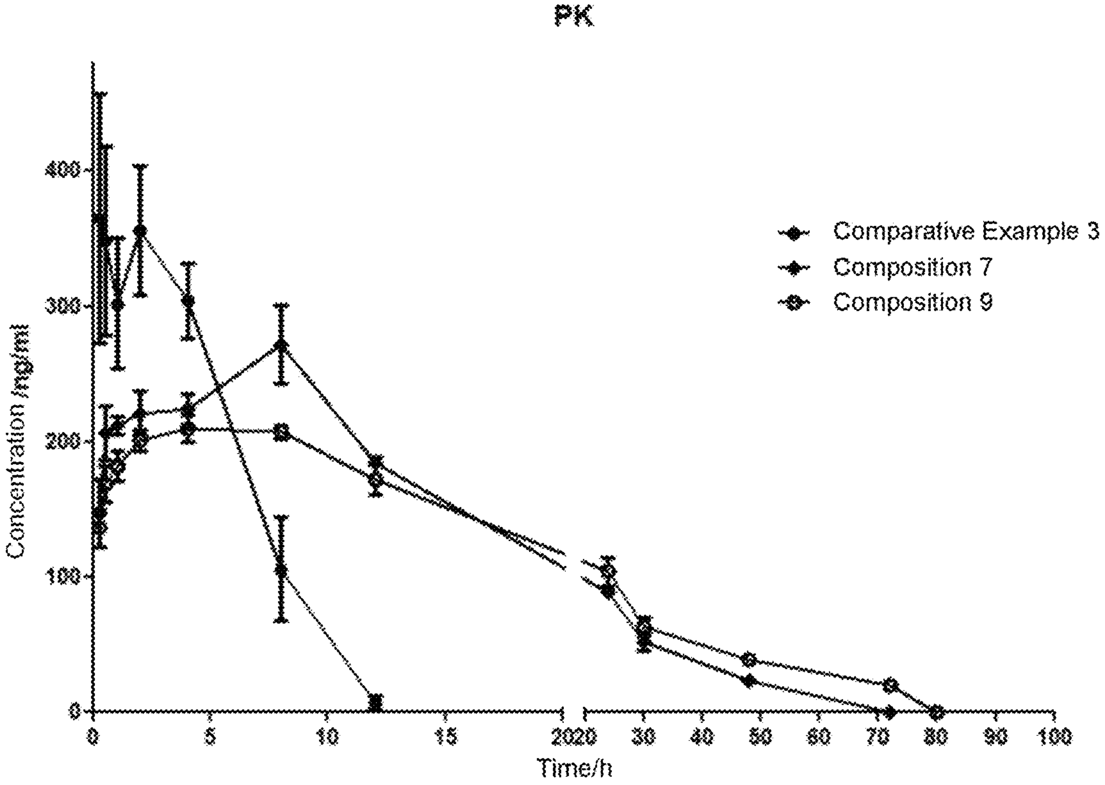
FIG. 7 and FIG. 8 show the results of in vivo pharmacokinetic (PK) investigation of the ropivacaine pharmaceutical compositions of the present invention (Compositions 7, 9, and 17) and Comparative Examples 3 and 4.
Figure 8:
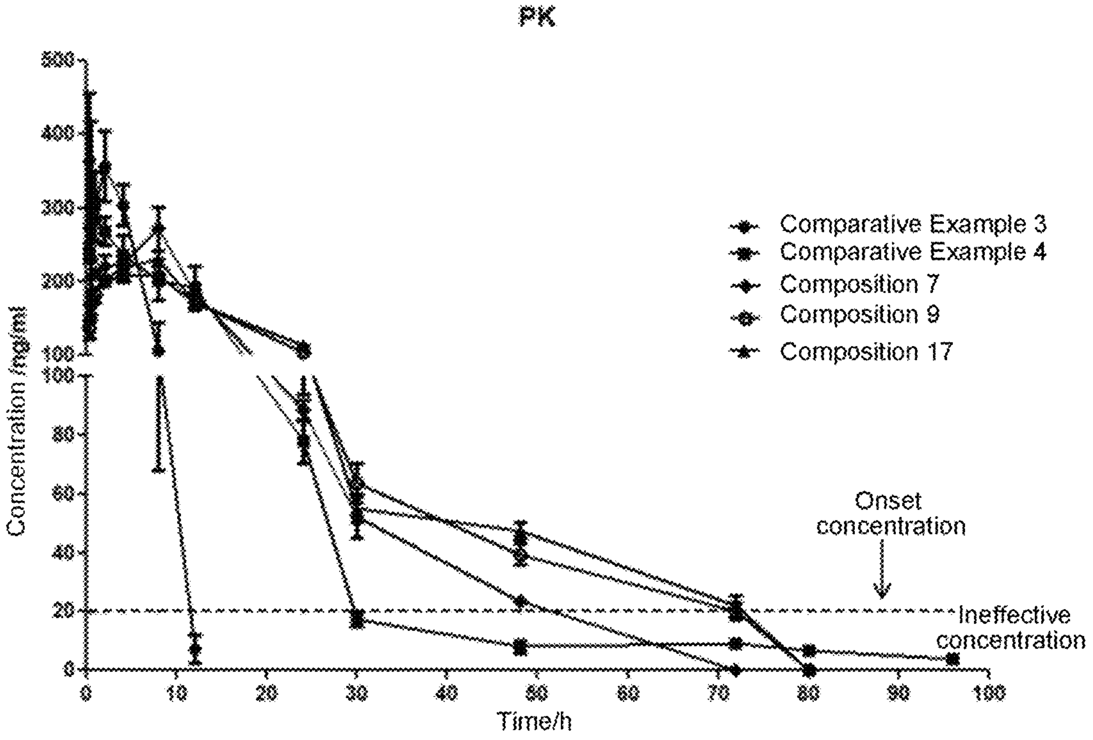

According to the results of the pharmacodynamic test of Experimental Example 3, because the composition of the present invention had a good correlation between plasma concentration and drug efficacy, and the duration of efficacy of compositions 7, 9, and 17 were 48 h, 72 h, and 72 h, respectively, it is inferred that the onset concentration of ropivacaine hydrochloride in rats was about 20 ng/ml (in Comparative Example 3, after injection into the body, the drug entered the blood rapidly, resulting in a poor correlation between its plasma concentration and local efficacy, so the onset concentration of 20 ng/ml was not applicable for Comparative Example 3). As shown in FIG. 7, the drug concentration below the onset concentration was the ineffective drug concentration, and the plasma concentration of Comparative Example 4 reached the ineffective concentration at about 30 h, and its overall bioavailability and effective bioavailability were low, indicating that part of its drug were failure to effectively exert its action and remain in the body for a long time at a low concentration, which would undoubtedly bring a higher risk of neurotoxicity. However, compared with Comparative Example 4, for Compositions 7, 9 and 17, the drug was fully exposed within the required time for analgesia (e.g. 48 h or 72 h), reducing the duration of the drug retention in the body in an ineffective form. Meanwhile, the bioavailability and effective bioavailability of Compositions 7, 9 and 17 were improved, indicating that the composition of the present invention was released more completely in the body, and the efficacy could be fully exerted, the drug utilization was improved, and the risk of neurotoxicity was reduced, and medication safety was improved.

To sum up, the composition of the present invention can reduce $C_{max}$ by at least 70% compared with Comparative Example 3 (ropivacaine hydrochloride injection) at the same dose. Compared with conventional sustained-release preparations, the composition of the present invention has more complete drug release, significantly improved bioavailability and effective bioavailability, can reduce the duration of drug retention in the body in an ineffective form, and improve drug utilization, and reduce the risk of toxicity due to prolonged exposure of nerve fibers to low drug concentrations. In addition, under the condition of having the same analgesic effect, the composition of the present invention can improve motor block and reduce neurotoxicity compared with conventional sustained-release preparations, which was of great significance in clinical use. In the case of a certain proportion, the efficacy enhancer in the present invention can exert unexpected effects.

Experimental Example 5

In the following experimental descriptions, the administered dose referred to the dose calculated according to the amount of the hydrochloride salt of the active ingredient in the preparation (i.e., in the case of using a free base, converted to hydrochloride salt).

Irritation Investigation at Injection Site

Figure 10:
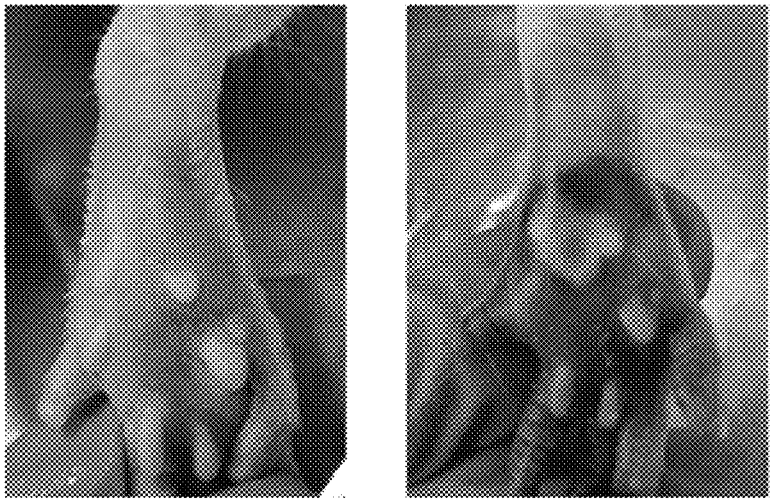
FIG. 10 shows the observation results of irritation of Composition 8 of the present invention and Comparative Example 7 at the injection site.

Composition 8 and Comparative Example 7 were respectively injected into the subcutaneous tissue of voix pedis in rats, and the irritation at the injection site was observed 24 hours after the administration. Dosing information was shown in Table 25, and results were shown in FIG. 10.

TABLE 25

Dosing Information of Compositions

| Composition | Dose |
|---|---|
| Composition 8 | 45 mg/kg |
| Comparative example 7 | 45 mg/kg |

It can be seen from the results that at 24 h after administration, the skin at the injection site of Comparative Example 7 was obviously blackened or even slightly ulcerated, showing greater irritation, and the injection site of the composition of the present invention had no obvious abnormality except for slight redness and swelling. It can be seen that the composition of the present invention had better injection site tolerance and safety compared with Comparative Example 7.

Experimental Example 6

In the following experimental descriptions, the administered dose referred to the dose calculated according to the amount of the hydrochloride salt of the active ingredient in the preparation (i.e., in the case of using a free base, converted to hydrochloride salt).

Histopathological Observation of Injection Site

Figure 11:
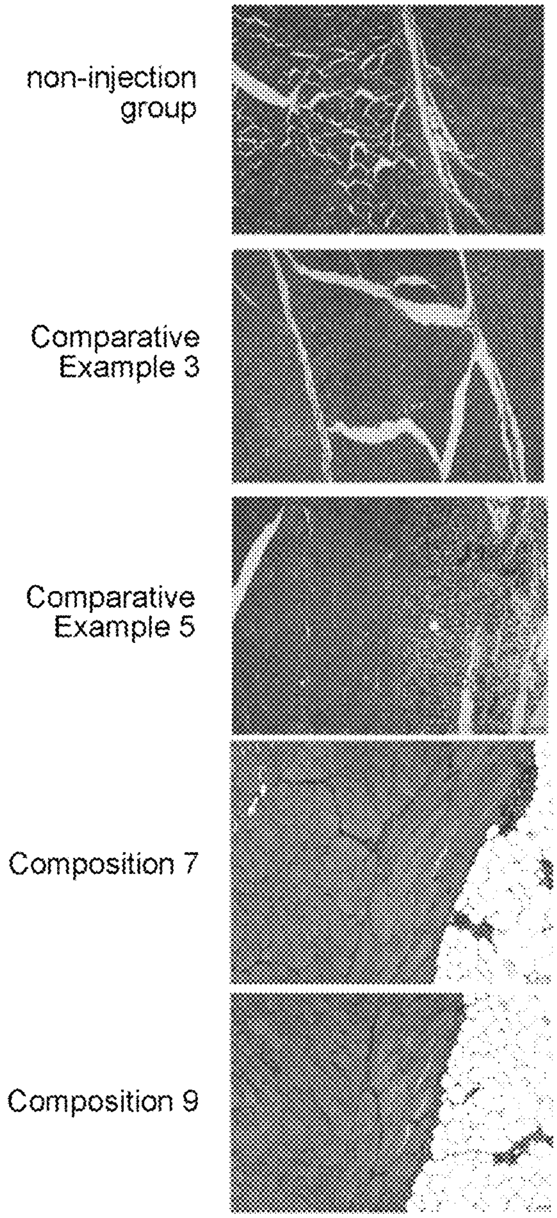
FIG. 11 shows the histopathological observation results at the injection site of the non-injection group, Comparative Example 3, Comparative Example 5 and the ropivacaine compositions of the present invention (Compositions 7 and 9).

Rats were subjected to subcutaneous injection of 13 mg/kg of Comparative Example 3, 45 mg/kg of Comparative Example 5, Composition 7 and Composition 9, and at 48 h after administration, the rats were euthanized, and tissue samples at the injection site were dissociated using a scalpel. The sample size should cover the tissue size of the administration site. After flushing with normal saline, the sample was fixed in buffered formalin. After dehydration treatment with the dehydrating agent xylene, the tissue samples were embedded in paraffin, cut into thin sections (5 μm tissue sections) using a cryostat, placed on glass slides, and stained with hematoxylin-eosin to obtain tissue sections. Histomorphology and immunohistology were observed under microscope. The results were shown in FIG. 11.

It can be seen from the results that there was no obvious abnormality in the tissue sections of Composition 7, Composition 9, non-injection group and Comparative Example 3, while obvious inflammatory cell infiltration occurred with serious irritation at the injection site in Comparative Example 5. It can be seen that the composition of the present invention had good safety and can reduce the irritation at the injection site compared with the conventional sustained-release preparation.

As reported in Acute Med Surg. 2017 April; 4(2): 152-160, for neurotoxicity, the inflammation and reactive fibrosis around nerve fibers near the administration site can be generally observed. In histopathological evaluation, it is mainly infiltration of infiltrating cells (including macrophages, foreign body giant cells, lymphocytes, and plasma cells). Compared with Comparative Example 5, the composition of the present invention significantly reduced the irritation reaction at the injection site, indicating that the composition of the present invention had a positive effect on reducing neurotoxicity.

What is claimed is:

1. A long-acting ropivacaine pharmaceutical composition comprising, based on the total weight of the composition, in weight percentage, 0.5% to 10% of ropivacaine;
2% to 25% of a pharmaceutical solvent;
8% to 55% of a pharmaceutical phospholipid;
15% to 89% of a pharmaceutical oil;
2% to 10% of an efficacy enhancer;
0% to 1% of an antioxidant; and
0% to 8% of an acid-base regulator, wherein the efficacy enhancer is one or more selected from substances having an eicosapentaenoic acid content of no less than 15% and a docosahexaenoic acid content of no less than 10%, or the efficacy enhancer is selected from linseed oil, *perilla* seed oil, walnut oil, argan oil, fish oil, layer oil and algal oil, and combinations thereof, wherein the pharmaceutical phospholipid is one or more selected from the group consisting of natural phospholipids, semi-synthetic phospholipids and synthetic phospholipids, wherein the natural phospholipid is selected from the group consisting of egg yolk lecithin, soybean phospholipid and combinations thereof, wherein the semi-synthetic phospholipid is selected from hydrogenated egg yolk lecithin, hydrogenated soybean phospholipid and combinations thereof, and wherein the synthetic phospholipid is one or more selected from the group consisting of dipalmitoyl phosphatidylethanolamine, dipalmitoyl phosphatidic acid, dipalmitoylphosphatidylglycerol, dioleoylphosphatidylethanolamine, dipalmitoylphosphatidylcholine, distearoylphosphatidyl-choline, and dimyristoylphosphatidylcholine.

2. The long-acting ropivacaine pharmaceutical composition according to claim 1, wherein the pharmaceutical composition reduces peak plasma concentration of a drug by 30% or more compared with ropivacaine hydrochloride injection at the same dose; and the pharmaceutical composition has a duration of action of 12 h or more.

3. The long-acting ropivacaine pharmaceutical composition according to claim 1, wherein the ropivacaine includes ropivacaine free base and salts thereof, wherein the pharmaceutical solvent is one or more selected from the group consisting of benzyl alcohol, ethanol, propylene glycol, glycerin, isopropanol, N-methylpyrrolidone, dimethyl sulfoxide, liquid polyethylene glycol, dimethylacetamide, glycerol monoacetate, polyethylene glycol monomethyl ether, diethylene glycol monoethyl ether, ethyl lactate, ethyl acetate, propylene glycol diethyl ester, diethyl malonate, tetrahydrofuran polyethylene glycol ether, and benzyl benzoate, wherein the antioxidant is one or more selected from the group consisting of cysteine, α-tocopherol, α-tocopherol acetate, N-acetyl-L-cysteine, butylated hydroxyanisole, dibutylated hydroxytoluene, propyl gallate, tert-butyl hydroquinone, lipoic acid, tea polyphenol, L-ascorbyl palmitate, and glutathione, wherein the acid-base regulator is one or more selected from the group consisting of arginine, lysine, histidine, glycine, tromethamine, diethanolamine, ethylenediamine, meglumine, hydrochloric acid, acetic acid, anhydrous citric acid, ascorbic acid, lactic acid, tartaric acid, methanesulfonic acid, methionine, sodium hydroxide, and triethanolamine, and wherein the pharmaceutical oil is one or more selected from the group consisting of natural vegetable oils, semi-natural oils artificially modified from natural vegetable oils, purified oils, and artificially synthesized oils.

4. The long-acting ropivacaine pharmaceutical composition according to claim 1, wherein the pharmaceutical solvent is one or more selected from the group consisting of benzyl alcohol, propylene glycol, and ethanol, wherein the antioxidant is one or more selected from the group consisting of α-tocopherol, L-ascorbyl palmitate, and cysteine, wherein the natural vegetable oils include castor oil, sesame oil, soybean oil, sunflower oil, peanut oil, corn oil, rapeseed oil, olive oil, and cottonseed oil, wherein the semi-natural oils artificially modified from natural vegetable oils include hydrogenated castor oil, wherein the artificially synthesized oils include medium chain triglycerides, long chain triglycerides, triacetin, and ethyl oleate.

5. A method of pain treatment comprising administering a pain relief medicament including the long-acting ropivacaine pharmaceutical composition according to claim 1.

6. The method according to claim 5, wherein the pain relief medicament is administered by local injection.

7. The method according to claim 5, wherein the expected total daily dose of the long-acting ropivacaine pharmaceutical composition is 5-1000 mg of the active drug.

8. The long-acting ropivacaine pharmaceutical composition according to claim 1, wherein the pharmaceutical composition has a duration of action of 24 h or more.

9. The long-acting ropivacaine pharmaceutical composition according to claim 1, wherein the pharmaceutical composition has a duration of action of 48 h or more.

10. The long-acting ropivacaine pharmaceutical composition according to claim 1, wherein the pharmaceutical composition comprises, based on the total weight of the composition, in weight percentage, 1% to 8% of ropivacaine;

3% to 23% of the pharmaceutical solvent;

10% to 50% of the pharmaceutical phospholipid;

20% to 76% of the pharmaceutical oil;

2% to 9% of the efficacy enhancer;

0% to 0.5% of the antioxidant; and

0% to 5% of the acid-base regulator.

11. The long-acting ropivacaine pharmaceutical composition according to claim 1, wherein the pharmaceutical composition comprises, based on the total weight of the composition, in weight percentage, 1% to 5% of ropivacaine;

5% to 20% of the pharmaceutical solvent;

15% to 45% of the pharmaceutical phospholipid;

22% to 60% of the pharmaceutical oil;

2% to 8% of the efficacy enhancer;

0% to 0.3% of the antioxidant; and

0% to 3% of the acid-base regulator.

12. The long-acting ropivacaine pharmaceutical composition according to claim 1, wherein the efficacy enhancer is substances having an eicosapentaenoic acid content of no less than 20% and a docosahexaenoic acid content of no less than 10%.

13. The method according to claim 5, wherein a pain treated is postoperative pain.

14. The method according to claim 6, wherein the local injection includes subcutaneous or intramuscular injection, direct instillation at the incision, incision infiltration, administration at the nerve plexus, and intra-articular injection.

* * * * *